(12) United States Patent
Mi et al.

(10) Patent No.: US 10,413,733 B2
(45) Date of Patent: Sep. 17, 2019

(54) IMPLANTABLE MEDICAL DEVICE WITH GYROSCOPE

(71) Applicant: CARDIAC PACEMAKERS, INC., St. Paul, MN (US)

(72) Inventors: Bin Mi, Plymouth, MN (US); Pramodsingh Hirasingh Thakur, Woodbury, MN (US); Jeffrey E. Stahmann, Ramsey, MN (US); Keith R. Maile, New Brighton, MN (US); Qi An, Blaine, MN (US); Brendan Early Koop, Ham Lake, MN (US); Yinghong Yu, Shoreview, MN (US); Viktoria A. Averina, Shoreview, MN (US); Michael J. Kane, St. Paul, MN (US); Krzysztof Z. Siejko, Maple Grove, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 12 days.

(21) Appl. No.: 15/791,286

(22) Filed: Oct. 23, 2017

(65) Prior Publication Data

US 2018/0117340 A1    May 3, 2018

Related U.S. Application Data

(60) Provisional application No. 62/413,787, filed on Oct. 27, 2016.

(51) Int. Cl.
*A61N 1/365* (2006.01)
*G06F 3/0346* (2013.01)
(Continued)

(52) U.S. Cl.
CPC ............ *A61N 1/36578* (2013.01); *A61B 5/00* (2013.01); *A61B 5/02028* (2013.01);
(Continued)

(58) Field of Classification Search
CPC ................ A61N 1/362; A61N 1/36542; A61N 1/36578; A61N 1/37205; A61N 1/37512; A61N 1/3756
See application file for complete search history.

(56) References Cited

U.S. PATENT DOCUMENTS

| 3,835,864 A | 9/1974 | Rasor et al. |
| 3,943,936 A | 3/1976 | Rasor et al. |

(Continued)

FOREIGN PATENT DOCUMENTS

| AU | 2008279789 B2 | 10/2011 |
| AU | 2008329620 B2 | 5/2014 |

(Continued)

OTHER PUBLICATIONS

US 8,886,318 B2, 11/2014, Jacobson et al. (withdrawn)
(Continued)

*Primary Examiner* — Allen Porter
(74) *Attorney, Agent, or Firm* — Seager, Tufte & Wickhem LLP.

(57) ABSTRACT

An implantable medical device (IMD) that includes a housing, a first electrode secured relative to the housing, a second electrode secured relative to the housing, and a gyroscope secured relative to the housing. The IMD may include circuitry in the housing in communication with the first electrode, the second electrode, and the gyroscope. The circuitry may be configured to determine and store a plurality of torsion data measurements, from which a representation of a twist profile may be determined.

20 Claims, 11 Drawing Sheets

(51) Int. Cl.

| | |
|---|---|
| *G01C 19/38* | (2006.01) |
| *A61N 1/375* | (2006.01) |
| *A61B 5/00* | (2006.01) |
| *A61B 5/02* | (2006.01) |
| *A61B 5/11* | (2006.01) |
| *A61N 1/372* | (2006.01) |
| *A61B 5/0205* | (2006.01) |
| *A61B 5/0215* | (2006.01) |
| *A61B 5/042* | (2006.01) |
| *A61B 5/0472* | (2006.01) |

(52) U.S. Cl.
CPC .......... *A61B 5/1121* (2013.01); *A61N 1/3756* (2013.01); *G01C 19/38* (2013.01); *G06F 3/0346* (2013.01); *A61B 5/0205* (2013.01); *A61B 5/0215* (2013.01); *A61B 5/042* (2013.01); *A61B 5/0472* (2013.01); *A61B 5/4839* (2013.01); *A61B 2562/0219* (2013.01); *A61N 1/37252* (2013.01)

(56) References Cited

U.S. PATENT DOCUMENTS

| | | |
|---|---|---|
| 4,142,530 A | 3/1979 | Wittkampf |
| 4,151,513 A | 4/1979 | Menken et al. |
| 4,157,720 A | 6/1979 | Greatbatch |
| RE30,366 E | 8/1980 | Rasor et al. |
| 4,243,045 A | 1/1981 | Maas |
| 4,250,884 A | 2/1981 | Hartlaub et al. |
| 4,256,115 A | 3/1981 | Bilitch |
| 4,263,919 A | 4/1981 | Levin |
| 4,310,000 A | 1/1982 | Lindemans |
| 4,312,354 A | 1/1982 | Walters |
| 4,323,081 A | 4/1982 | Wiebusch |
| 4,357,946 A | 11/1982 | Dutcher et al. |
| 4,365,639 A | 12/1982 | Goldreyer |
| 4,440,173 A | 4/1984 | Hudziak et al. |
| 4,476,868 A | 10/1984 | Thompson |
| 4,522,208 A | 6/1985 | Buffet |
| 4,537,200 A | 8/1985 | Widrow |
| 4,556,063 A | 12/1985 | Thompson et al. |
| 4,562,841 A | 1/1986 | Brockway et al. |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,776,338 A | 10/1988 | Lekholm et al. |
| 4,787,389 A | 11/1988 | Tarjan |
| 4,793,353 A | 12/1988 | Borkan |
| 4,819,662 A | 4/1989 | Heil et al. |
| 4,858,610 A | 8/1989 | Callaghan et al. |
| 4,886,064 A | 12/1989 | Strandberg |
| 4,887,609 A | 12/1989 | Cole |
| 4,928,688 A | 5/1990 | Mower |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,058,581 A | 10/1991 | Silvian |
| 5,078,134 A | 1/1992 | Heilman et al. |
| 5,109,845 A | 5/1992 | Yuuchi et al. |
| 5,113,859 A | 5/1992 | Funke |
| 5,113,869 A | 5/1992 | Nappholz et al. |
| 5,117,824 A | 6/1992 | Keimel et al. |
| 5,127,401 A | 7/1992 | Grevious et al. |
| 5,133,353 A | 7/1992 | Hauser |
| 5,144,950 A | 9/1992 | Stoop et al. |
| 5,170,784 A | 12/1992 | Ramon et al. |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,259,387 A | 11/1993 | DePinto |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,305,760 A | 4/1994 | McKown et al. |
| 5,312,439 A | 5/1994 | Loeb |
| 5,313,953 A | 5/1994 | Yomtov et al. |
| 5,314,459 A | 5/1994 | Swanson et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | deCoriolis et al. |
| 5,370,667 A | 12/1994 | Alt |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,571,146 A | 11/1996 | Jones et al. |
| 5,591,214 A | 1/1997 | Lu |
| 5,620,466 A | 4/1997 | Haefner et al. |
| 5,634,938 A | 6/1997 | Swanson et al. |
| 5,649,968 A | 7/1997 | Alt et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,706,823 A | 1/1998 | Wodlinger |
| 5,709,215 A | 1/1998 | Perttu et al. |
| 5,720,770 A | 2/1998 | Nappholz et al. |
| 5,728,154 A | 3/1998 | Crossett et al. |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,759,199 A | 6/1998 | Snell et al. |
| 5,774,501 A | 6/1998 | Halpern et al. |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,814,089 A | 9/1998 | Stokes et al. |
| 5,827,216 A | 10/1998 | Igo et al. |
| 5,836,985 A | 11/1998 | Rostami et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |
| 5,935,078 A | 8/1999 | Feierbach |
| 5,941,906 A | 8/1999 | Barreras, Sr. et al. |
| 5,944,744 A | 8/1999 | Paul et al. |

(56) References Cited

U.S. PATENT DOCUMENTS

| | | |
|---|---|---|
| 5,954,757 A | 9/1999 | Gray |
| 5,978,713 A | 11/1999 | Prutchi et al. |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,016,445 A | 1/2000 | Baura |
| 6,026,320 A | 2/2000 | Carlson et al. |
| 6,029,085 A | 2/2000 | Olson et al. |
| 6,041,250 A | 3/2000 | DePinto |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |
| 6,128,526 A | 10/2000 | Stadler et al. |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 6,990,375 B2 | 1/2006 | Kloss et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |

(56) References Cited

U.S. PATENT DOCUMENTS

| | | |
|---|---|---|
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,321,798 B2 | 1/2008 | Muhlenberg et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,445,605 B2 | 11/2008 | Overall et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hübinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |

(56) References Cited

U.S. PATENT DOCUMENTS

| | | |
|---|---|---|
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,079 B2 | 10/2011 | Bange et al. |
| 8,046,080 B2 | 10/2011 | Von Arx et al. |
| 8,050,297 B2 | 11/2011 | DelMain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,262,578 B1 | 9/2012 | Bharmi et al. |
| 8,265,748 B2 | 9/2012 | Liu et al. |
| 8,265,757 B2 | 9/2012 | Mass et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,280 B2 | 1/2014 | Allavatam et al. |
| 8,626,294 B2 | 1/2014 | Sheldon et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |

(56) References Cited

U.S. PATENT DOCUMENTS

| | | |
|---|---|---|
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,868,186 B2 | 10/2014 | Kroll |
| 8,886,339 B2 | 11/2014 | Faltys et al. |
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Régnier et al. |
| 9,457,193 B2 | 10/2016 | Klimovitch et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 9,522,276 B2 | 12/2016 | Shen et al. |
| 9,522,280 B2 | 12/2016 | Fishler et al. |
| 9,526,522 B2 | 12/2016 | Wood et al. |
| 9,526,891 B2 | 12/2016 | Eggen et al. |
| 9,526,909 B2 | 12/2016 | Stahmann et al. |
| 9,533,163 B2 | 1/2017 | Klimovitch et al. |
| 9,561,382 B2 | 2/2017 | Persson et al. |
| 9,566,012 B2 | 2/2017 | Greenhut et al. |
| 9,636,511 B2 | 5/2017 | Carney et al. |
| 9,669,223 B2 | 6/2017 | Auricchio et al. |
| 9,687,654 B2 | 6/2017 | Sheldon et al. |
| 9,687,655 B2 | 6/2017 | Pertijs et al. |
| 9,687,659 B2 | 6/2017 | Von Arx et al. |
| 9,694,186 B2 | 7/2017 | Carney et al. |
| 9,782,594 B2 | 10/2017 | Stahmann et al. |
| 9,782,601 B2 | 10/2017 | Ludwig |
| 9,789,317 B2 | 10/2017 | Greenhut et al. |
| 9,789,319 B2 | 10/2017 | Sambelashvili |
| 9,808,617 B2 | 11/2017 | Ostroff et al. |
| 9,808,628 B2 | 11/2017 | Sheldon et al. |
| 9,808,631 B2 | 11/2017 | Maile et al. |
| 9,808,632 B2 | 11/2017 | Reinke et al. |
| 9,808,633 B2 | 11/2017 | Bonner et al. |
| 9,808,637 B2 | 11/2017 | Sharma et al. |
| 9,855,414 B2 | 1/2018 | Marshall et al. |
| 9,855,430 B2 | 1/2018 | Ghosh et al. |
| 9,855,435 B2 | 1/2018 | Sahabi et al. |
| 9,861,815 B2 | 1/2018 | Tran et al. |
| 10,080,887 B2 | 9/2018 | Schmidt et al. |
| 10,080,888 B2 | 9/2018 | Kelly et al. |
| 10,080,900 B2 | 9/2018 | Ghosh et al. |
| 10,080,903 B2 | 9/2018 | Willis et al. |
| 10,086,206 B2 | 10/2018 | Sambelashvili |
| 10,118,026 B2 | 11/2018 | Grubac et al. |
| 10,124,163 B2 | 11/2018 | Ollivier et al. |
| 10,124,175 B2 | 11/2018 | Berthiaume et al. |
| 10,130,821 B2 | 11/2018 | Grubac et al. |
| 10,137,305 B2 | 11/2018 | Kane et al. |
| 10,159,842 B2 * | 12/2018 | Kane .................. A61N 1/3704 |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0088278 A1 | 5/2003 | Bardy et al. |

(56) References Cited

U.S. PATENT DOCUMENTS

| | | |
|---|---|---|
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0230283 A1 | 11/2004 | Prinzen et al. |
| 2004/0249431 A1 | 12/2004 | Ransbury et al. |
| 2004/0260346 A1 | 12/2004 | Overall et al. |
| 2004/0260348 A1 | 12/2004 | Bakken et al. |
| 2004/0267303 A1 | 12/2004 | Guenst |
| 2005/0043651 A1* | 2/2005 | Elle .............. A61B 5/0031 600/595 |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Von Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0032749 A1 | 2/2007 | Overall et al. |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0294229 A1 | 11/2008 | Friedman et al. |
| 2008/0306359 A1 | 12/2008 | Zdeblick et al. |
| 2009/0005829 A1* | 1/2009 | Mi .............. A61B 5/02438 607/17 |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |
| 2009/0210024 A1 | 8/2009 | M. |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0266573 A1 | 10/2009 | Engmark et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0069983 A1 | 3/2010 | Peacock, III et al. |
| 2010/0094367 A1 | 4/2010 | Sen |

(56) References Cited

U.S. PATENT DOCUMENTS

| | | |
|---|---|---|
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0298841 A1 | 11/2010 | Prinzen et al. |
| 2010/0312309 A1 | 12/2010 | Harding |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0270341 A1 | 11/2011 | Ruben et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Dal Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0245665 A1 | 9/2012 | Friedman et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0289776 A1 | 11/2012 | Keast et al. |
| 2012/0289815 A1 | 11/2012 | Keast et al. |
| 2012/0290021 A1 | 11/2012 | Saurkar et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0192611 A1 | 8/2013 | Taepke, II et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253309 A1 | 9/2013 | Allan et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |

(56) References Cited

U.S. PATENT DOCUMENTS

| | | |
|---|---|---|
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100624 A1 | 4/2014 | Ellingson |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222015 A1 | 8/2014 | Keast et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0343348 A1 | 11/2014 | Kaplan et al. |
| 2014/0371818 A1 | 12/2014 | Bond et al. |
| 2014/0379041 A1 | 12/2014 | Foster |
| 2015/0025612 A1 | 1/2015 | Haasl et al. |
| 2015/0039041 A1 | 2/2015 | Smith et al. |
| 2015/0045868 A1 | 2/2015 | Bonner et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0126854 A1 | 5/2015 | Keast et al. |
| 2015/0157861 A1 | 6/2015 | Aghassian |
| 2015/0157866 A1 | 6/2015 | Demmer et al. |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0230699 A1 | 8/2015 | Berul et al. |
| 2015/0238769 A1 | 8/2015 | Demmer et al. |
| 2015/0258345 A1 | 9/2015 | Smith et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306401 A1 | 10/2015 | Demmer et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2015/0335884 A1 | 11/2015 | Khairkhahan et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0144192 A1 | 5/2016 | Sanghera et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0317825 A1 | 11/2016 | Jacobson |
| 2016/0367823 A1 | 12/2016 | Cowan et al. |
| 2017/0014629 A1 | 1/2017 | Ghosh et al. |
| 2017/0035315 A1 | 2/2017 | Jackson |
| 2017/0043173 A1 | 2/2017 | Sharma et al. |
| 2017/0043174 A1 | 2/2017 | Greenhut et al. |
| 2017/0056649 A1* | 3/2017 | Kane .................. A61N 1/08 |
| 2017/0056664 A1* | 3/2017 | Kane .................. A61N 1/378 |
| 2017/0056668 A1* | 3/2017 | Maile ............. A61N 1/36585 |
| 2017/0056671 A1* | 3/2017 | Kane ................ A61N 1/3704 |
| 2017/0189681 A1 | 7/2017 | Anderson |
| 2017/0281261 A1 | 10/2017 | Shuros et al. |
| 2017/0281952 A1 | 10/2017 | Shuros et al. |
| 2017/0281953 A1 | 10/2017 | Min et al. |
| 2017/0281955 A1 | 10/2017 | Maile et al. |
| 2017/0312531 A1 | 11/2017 | Sawchuk |
| 2018/0117304 A1* | 5/2018 | Koop .................. A61B 5/0031 |
| 2018/0256902 A1 | 9/2018 | Toy et al. |
| 2018/0256909 A1 | 9/2018 | Smith et al. |
| 2018/0264262 A1 | 9/2018 | Haasl et al. |
| 2018/0264270 A1 | 9/2018 | Koop et al. |
| 2018/0264272 A1 | 9/2018 | Haasl et al. |
| 2018/0264273 A1 | 9/2018 | Haasl et al. |
| 2018/0264274 A1 | 9/2018 | Haasl et al. |
| 2018/0279897 A1* | 10/2018 | Eddy .................. A61B 5/0456 |
| 2018/0339160 A1 | 11/2018 | Carroll |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |
| EP | 0362611 A1 | 4/1990 |
| EP | 503823 A2 | 9/1992 |
| EP | 1702648 A2 | 9/2006 |
| EP | 1458290 B1 | 4/2009 |
| EP | 1904166 B1 | 6/2011 |
| EP | 2471452 A1 | 7/2012 |
| EP | 2433675 B1 | 1/2013 |
| EP | 2441491 B1 | 1/2013 |
| EP | 2452721 B1 | 11/2013 |
| EP | 2662113 A3 | 11/2013 |
| EP | 1948296 B1 | 1/2014 |
| EP | 2760541 B1 | 5/2016 |
| EP | 2833966 B1 | 5/2016 |
| JP | 2000051373 A | 2/2000 |
| JP | 2002502640 A | 1/2002 |
| JP | 2004512105 A | 4/2004 |
| JP | 2005508208 A | 3/2005 |

(56) References Cited

FOREIGN PATENT DOCUMENTS

| | | |
|---|---|---|
| JP | 2005245215 A | 9/2005 |
| JP | 2006518631 A | 8/2006 |
| JP | 2008540040 A | 11/2008 |
| JP | 5199867 B2 | 2/2013 |
| WO | 9500202 A1 | 1/1995 |
| WO | 9636134 A1 | 11/1996 |
| WO | 9724981 A2 | 7/1997 |
| WO | 9826840 A1 | 6/1998 |
| WO | 9939767 A1 | 8/1999 |
| WO | 0234330 A2 | 5/2002 |
| WO | 02098282 A2 | 12/2002 |
| WO | 2004066825 A2 | 8/2004 |
| WO | 2005000206 A3 | 1/2005 |
| WO | 2005042089 A1 | 5/2005 |
| WO | 2006065394 A1 | 6/2006 |
| WO | 2006086435 A3 | 8/2006 |
| WO | 2006113659 A1 | 10/2006 |
| WO | 2006124833 A3 | 11/2006 |
| WO | 2007073435 A1 | 6/2007 |
| WO | 2007075974 A2 | 7/2007 |
| WO | 2009006531 A1 | 1/2009 |
| WO | 2012054102 A1 | 4/2012 |
| WO | 2013080038 A2 | 6/2013 |
| WO | 2013098644 A3 | 7/2013 |
| WO | 2013121431 A1 | 8/2013 |
| WO | 2013184787 A1 | 12/2013 |
| WO | 2014120769 A1 | 8/2014 |

OTHER PUBLICATIONS

"Instructions for Use System 1, Leadless Cardiac Pacemaker (LCP) and Delivery Catheter," Nanostim Leadless Pacemakers, pp. 1-28, 2013.
Hachisuka et al., "Development and Performance Analysis of an Intra-Body Communication Device," The 12th International Conference on Solid State Sensors, Actuators and Microsystems, vol. 4A1.3, pp. 1722-1725, 2003.
Seyedi et al., "A Survey on Intrabody Communications for Body Area Network Application," IEEE Transactions on Biomedical Engineering,vol. 60(8): 2067-2079, 2013.
Spickler et al., "Totally Self-Contained Intracardiac Pacemaker," Journal of Electrocardiology, vol. 3(3&4): 324-331, 1970.
Wegmüller, "Intra-Body Communication for Biomedical Sensor Networks," Diss. ETH, No. 17323, 1-173, 2007.
Abozguia et al., "Left ventricular strain and untwist in hypertrophic cardiomyopathy: Relation to exercise capacity," American Heart Journal,159: pp. 825-832, May 2010.
Bertini et al., "Role of Left Ventricular Twist Mechanics in the Assessment of Cardiac Dyssynchrony in Heart Failure," JACC: Cardiovascular Imaging, 2(12): pp. 1425-1435.
Dong et al., "MRI assessment of LV relaxation by untwisting rate: a new isovolumic phase measure of T," Am J Physiol Heart Circ Physiol, 281: pp. (H2002-H2009), Jul. 18, 2001.
Ingels et al., "Measurement of Midwall Myocardial Dynamics in Intact Man by Radiography of Surgically Implanted Markers," Circulation, (52): pp. 859-864, Nov. 1975.
Moral et al., "Left Ventricular Twist Mechanics in Hypertrophic Cardiomyopathy Assessed by Three-Dimensional Speckle Tracking Echocardiography," Cardiovascular Imaging and Hemodynamic Laboratory, pp. 1788-1795, 2011.
Notomi et al., "Ventricular untwisting: a temporal link between left ventricular relaxation and suction," Am J Physiol Heart Circ Physiol, (294): pp. H505-H513, Nov. 21, 2007.
Sengupta et al., "Twist Mechanics of the Left Ventricle: Principles and Applicaton," American College of Cardiology Foundation, 1(3): pp. 366-376, May 2008.
Nakatani, "Left Ventricular Rotation and Twist: Why Should We Learn?" Korean Society of Echocardiography, 19(1): pp. 1-6, 2011.
Wang et al., "Left Ventricular Untwisting Rate by Speckle Tracking Echocardiography," Circulation, 116: pp. 2580-2586, 2007.

\* cited by examiner

IMPLANTABLE MEDICAL DEVICE WITH GYROSCOPE

CROSS REFERENCE TO RELATED APPLICATIONS

This application claims the benefit of U.S. Provisional Patent Application Ser. No. 62/413,787 filed on Oct. 27, 2016, the disclosure of which is incorporated herein by reference.

TECHNICAL FIELD

The present disclosure generally relates to implantable medical devices and more particularly to implantable medical devices with a gyroscope

BACKGROUND

Implantable medical devices are commonly used to perform a variety of functions, such as to monitor one or more conditions and/or delivery therapy to a patient. In some cases, an implantable medical device may deliver neurostimulation therapy to a patient. In some cases, an implantable medical device may simply monitor one or more conditions, such as pressure, acceleration, cardiac events, and may communicate the detected conditions or events to another device, such as another implantable medical device or an external programmer.

In some cases, an implantable medical device may be configured to deliver pacing and/or defibrillation therapy to a patient. Such implantable medical devices may treat patients suffering from various heart conditions that may result in a reduced ability of the heart to deliver sufficient amounts of blood to a patient's body. In some cases, heart conditions may lead to rapid, irregular, and/or inefficient heart contractions. To help alleviate some of these conditions, various devices (e.g., pacemakers, defibrillators, etc.) may be implanted into a patient's body. When so provided, such devices can monitor and provide therapy, such as electrical stimulation therapy, to the patient's heart to help the heart operate in a more normal, efficient and/or safe manner. In some cases, a patient may have multiple implanted devices that cooperate to monitor and/or provide therapy to the patient's heart.

SUMMARY

The present disclosure generally relates to implantable medical devices and more particularly to implantable medical devices with gyroscopes.

In a first example, a leadless cardiac pacemaker (LCP) configured to sense cardiac activity and to pace a patient's heart may comprise a housing, an electrode secured relative to the housing and exposed to the environment outside of the housing, a gyroscope disposed relative to the housing, and circuitry in the housing in communication with the electrode and the gyroscope. The circuitry may be configured to generate a twisting profile over one or more cardiac cycles. The circuitry may be further configured to update one or more pacing parameters of the LCP based at least in part on the twisting profile and pace the patient's heart using one or more of the updated pacing parameters.

Alternatively or additionally to any of the examples above, in another example, the circuitry may be configured to update the twisting profile at a predefined regular interval.

Alternatively or additionally to any of the examples above, in another example, the circuitry may be configured to update the twisting profile in response to a detected condition change.

Alternatively or additionally to any of the examples above, in another example, the detected condition change may correspond to one of exercise, heart failure status, therapy modification (e.g., medication), cardiac status, pacing status, or posture.

Alternatively or additionally to any of the examples above, in another example, updating the one or more pacing parameters of the LCP may comprise adjusting an AV delay.

Alternatively or additionally to any of the examples above, in another example, updating the one or more pacing parameters of the LCP may comprise adjusting a VV delay.

Alternatively or additionally to any of the examples above, in another example, updating the one or more pacing parameters of the LCP may comprise a selection of different pacing vector.

Alternatively or additionally to any of the examples above, in another example, the circuitry may be further configured to compare (e.g., correlate) the twisting profile to an additional parameter to determine if the twisting profile is abnormal.

Alternatively or additionally to any of the examples above, in another example, the additional parameter may be one or more of a cardiovascular (e.g., ventricular) pressure, a heart sound, an ECG attribute (e.g., QRS width), a blood flow, impedance, respiration, and/or one or more cardiac dimensions.

In another example, a medical device system may comprise a first implantable medical device including a gyroscope, the first implantable medical device configured to be secured to a patient's heart and a second medical device. The first implantable medical device and/or the second medical device may be configured to determine a twisting profile of the patient's heart based at least in part on an output of the gyroscope, adjust one or more therapy parameters of a therapy based at least in part on the twisting profile, and deliver the therapy using one or more of the adjusted therapy parameters.

Alternatively or additionally to any of the examples above, in another example, the twisting profile may comprise a twist velocity, a twist vector, a twist angle, and their temporal progression related to the cardiac cycle. The twist vector can be defined as the axis normal to the plane of the twist.

Alternatively or additionally to any of the examples above, in another example, the twisting profile may provide confirmation of an event detected by the second medical device.

Alternatively or additionally to any of the examples above, in another example, the first implantable medical device and/or the second medical device may be further configured to update the twisting profile at a predefined regular interval.

Alternatively or additionally to any of the examples above, in another example, the first implantable medical device and/or the second medical device may be further configured to update the twisting profile in response to a detected condition change.

Alternatively or additionally to any of the examples above, in another example, the detected condition change may correspond to one of exercise, heart failure status, or posture.

Alternatively or additionally to any of the examples above, in another example, the first implantable medical device and/or the second medical device may be further configured to correlate the twisting profile to an additional parameter to determine if the twisting profile is abnormal.

In another example, a method for monitoring cardiac dysfunction of a patient's heart may comprise determining one or more twisting parameters of the patient's heart based at least in part on an output of a gyroscope secured relative to the patient's heart, adjusting a therapy for the patient's heart based at least in part on the one or more twisting parameters, and delivering the adjusted therapy to the patient's heart.

Alternatively or additionally to any of the examples above, in another example, the one or more twisting parameters may include at least one of a twist angle, a twist vector and a twist velocity, all related to the timing of a cardiac cycle.

Alternatively or additionally to any of the examples above, in another example, adjusting a therapy may comprise adjusting an implant location of a therapy delivering device.

Alternatively or additionally to any of the examples above, in another example, adjusting a therapy may comprise adjusting an AV delay.

Alternatively or additionally to any of the examples above, in another example, adjusting a therapy may comprise adjusting a VV delay.

Alternatively or additionally to any of the examples above, in another example, adjusting a therapy may comprise delivering an ATP therapy when the one or more twisting parameters indicate a tachyarrhythmia that is treatable with ATP therapy.

Alternatively or additionally to any of the examples above, in another example, adjusting a therapy may comprise altering a medication either via a direct action of a person or via a worn or implanted drug delivery device.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which.

Figure 1:
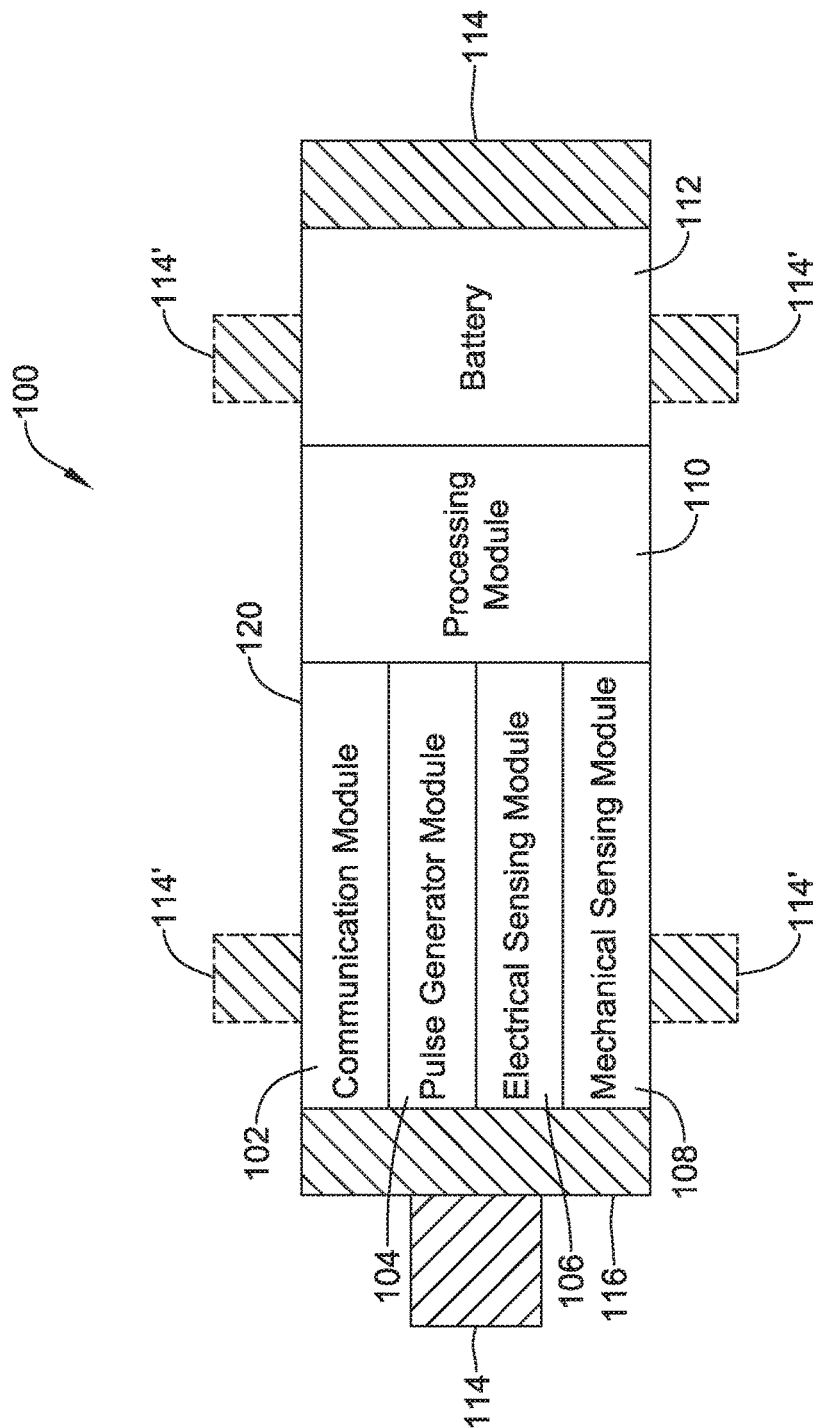
FIG. 1 is a schematic block diagram of an illustrative leadless cardiac pacemaker (LCP) according to one example of the present disclosure.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure. While the present disclosure is applicable to any suitable implantable medical device (IMD), the description below uses pacemakers and more particularly leadless cardiac pacemakers (LCP) as particular examples.

A normal, healthy heart induces contraction by conducting intrinsically generated electrical signals throughout the heart. These intrinsic signals cause the muscle cells or tissue of the heart to contract. This contraction forces blood out of and into the heart, providing circulation of the blood throughout the rest of the body. However, many patients suffer from cardiac conditions that affect this contractility of their hearts. For example, some hearts may develop diseased tissues that no longer generate or conduct intrinsic electrical signals. In some examples, diseased cardiac tissues conduct electrical signals at differing rates, thereby causing an unsynchronized and inefficient contraction of the heart. In other examples, a heart may initiate intrinsic signals at such a low rate that the heart rate becomes dangerously low. In still other examples, a heart may generate electrical signals at an unusually high rate. In some cases such an abnormality can develop into a fibrillation state, where the contraction of the patient's heart chambers are almost completely desynchronized and the heart pumps very little to no blood. Implantable medical devices, which may be configured to determine occurrences of such cardiac abnormalities or arrhythmias and deliver one or more types of electrical stimulation therapy to patient's hearts, may help to terminate or alleviate these and other cardiac conditions.

FIG. 1 depicts an illustrative leadless cardiac pacemaker (LCP) that may be implanted into a patient and may operate to prevent, control, or terminate cardiac arrhythmias in patients by, for example, appropriately employing one or more therapies (e.g. anti-tachycardia pacing (ATP) therapy, cardiac resynchronization therapy (CRT), bradycardia therapy, defibrillation pulses, or the like). As can be seen in FIG. 1, the LCP 100 may be a compact device with all components housed within the LCP 100 or directly on the housing 120. In the example shown in FIG. 1, the LCP 100 may include a communication module 102, a pulse generator module 104, an electrical sensing module 106, a mechanical sensing module 108, a processing module 110, a battery 112, and electrodes 114. The LCP 100 may include more or less modules, depending on the application.

The communication module 102 may be configured to communicate with devices such as sensors, other medical devices, and/or the like, that are located externally to the LCP 100. Such devices may be located either external or internal to the patient's body. Irrespective of the location, remote devices (i.e. external to the LCP 100 but not necessarily external to the patient's body) can communicate with the LCP 100 via the communication to module 102 to accomplish one or more desired functions. For example, the LCP 100 may communicate information, such as sensed electrical signals, data, instructions, messages, etc., to an external medical device through the communication module 102. The external medical device may use the communicated signals, data, instructions and/or messages to perform various functions, such as determining occurrences of arrhythmias, delivering electrical stimulation therapy, storing received data, analyzing received data, and/or performing any other suitable function. The LCP 100 may additionally receive information such as signals, data, instructions and/or messages from the external medical device through the communication module 102, and the LCP 100 may use the received signals, data, instructions and/or messages to perform various functions, such as determining occurrences of arrhythmias, delivering electrical stimulation therapy, storing received data, analyzing received data, and/or performing any other suitable function. The communication module 102 may be configured to use one or more methods for communicating with remote devices. For example, the communication module 102 may communicate via radiofrequency (RF) signals, inductive coupling, optical signals, acoustic signals, conducted communication signals, and/or any other signals suitable for communication.

In the example shown in FIG. 1, the pulse generator module 104 may be electrically connected to the electrodes 114. In some examples, the LCP 100 may include one or more additional electrodes 114'. In such examples, the pulse generator 104 may also be electrically connected to the additional electrodes 114'. The pulse generator module 104 may be configured to generate electrical stimulation signals. For example, the pulse generator module 104 may generate electrical stimulation signals by using energy stored in a battery 112 within the LCP 100 and deliver the generated electrical stimulation signals via the electrodes 114 and/or 114'. Alternatively, or additionally, the pulse generator 104 may include one or more capacitors, and the pulse generator 104 may charge the one or more capacitors by drawing energy from the battery 112. The pulse generator 104 may then use the energy of the one or more capacitors to deliver the generated electrical stimulation signals via the electrodes 114 and/or 114'. In at least some examples, the pulse generator 104 of the LCP 100 may include switching circuitry to selectively connect one or more of the electrodes 114 and/or 114' to the pulse generator 104 in order to select which of the electrodes 114/114' (and/or other electrodes) the pulse generator 104 delivers the electrical stimulation therapy. The pulse generator module 104 may generate electrical stimulation signals with particular features or in particular sequences in order to provide one or multiple of a number of different stimulation therapies. For example, the pulse generator module 104 may be configured to generate electrical stimulation signals to provide electrical stimulation therapy to combat bradycardia, tachycardia, cardiac dyssynchrony, bradycardia arrhythmias, tachycardia arrhythmias, fibrillation arrhythmias, cardiac synchronization arrhythmias and/or to produce any other suitable electrical stimulation therapy. Some more common electrical stimulation therapies include bradycardia therapy, anti-tachycardia pacing (ATP) therapy, cardiac resynchronization therapy (CRT), and cardioversion/defibrillation therapy.

In some examples, the LCP 100 may not include a pulse generator 104 or may turn off the pulse generator 104. When so provided, the LCP 100 may be a diagnostic only device. In such examples, the LCP 100 may not deliver electrical stimulation therapy to a patient. Rather, the LCP 100 may collect data about cardiac electrical activity and/or physiological parameters of the patient and communicate such data and/or determinations to one or more other medical devices via the communication module 102.

In some examples, the LCP 100 may include an electrical sensing module 106, and in some cases, a mechanical sensing module 108. The electrical sensing module 106 may be configured to sense the cardiac electrical activity of the heart. For example, the electrical sensing module 106 may be connected to the electrodes 114/114', and the electrical sensing module 106 may be configured to receive cardiac electrical signals conducted through the electrodes 114/114'. The cardiac electrical signals may represent local information from the chamber in which the LCP 100 is implanted. For instance, if the LCP 100 is implanted within a ventricle of the heart, cardiac electrical signals sensed by the LCP 100 through the electrodes 114/114' may represent ventricular cardiac electrical signals. The mechanical sensing module 108 may include one or more sensors, such as an accelerometer, a gyroscope, a blood pressure sensor, a heart sound sensor, a blood-oxygen sensor, a temperature sensor, a flow sensor and/or any other suitable sensors that are configured to measure one or more mechanical and/or chemical parameters of the patient. Both the electrical sensing module 106 and the mechanical sensing module 108 may be connected to a processing module 110, which may provide signals representative of the sensed mechanical parameters. Although described with respect to FIG. 1 as separate sensing modules, in some cases, the electrical sensing module 106 and the mechanical sensing module 108 may be combined into a single sensing module, as desired.

The electrodes 114/114' can be secured relative to the housing 120 but exposed to the tissue and/or blood surrounding the LCP 100. In some cases, the electrodes 114 may be generally disposed on either end of the LCP 100 and may be in electrical communication with one or more of the modules 102, 104, 106, 108, and 110. The electrodes 114/114' may be supported by the housing 120, although in some examples, the electrodes 114/114' may be connected to the housing 120 through short connecting wires such that the electrodes 114/114' are not directly secured relative to the housing 120. In examples where the LCP 100 includes one or more electrodes 114', the electrodes 114' may in some cases be disposed on the sides of the LCP 100, which may increase the number of electrodes by which the LCP 100 may sense cardiac electrical activity, deliver electrical stimulation and/or communicate with an external medical device. The electrodes 114/114' can be made up of one or more biocompatible conductive materials such as various metals or alloys that are known to be safe for implantation within a human body. In some instances, the electrodes 114/114' connected to LCP 100 may have an insulative portion that electrically isolates the electrodes 114/114' from adjacent electrodes, the housing 120, and/or other parts of the LCP 100.

The processing module 110 can be configured to control the operation of the LCP 100. For example, the processing module 110 may be configured to receive electrical signals from the electrical sensing module 106 and/or the mechanical sensing module 108. Based on the received signals, the processing module 110 may determine, for example, occurrences and, in some cases, types of arrhythmias. Based on any determined arrhythmias, the processing module 110 may control the pulse generator module 104 to generate electrical stimulation in accordance with one or more therapies to treat the determined arrhythmia(s). The processing module 110 may further receive information from the communication module 102. In some examples, the processing module 110 may use such received information to help determine whether an arrhythmia is occurring, determine a type of arrhythmia, and/or to take particular action in response to the information. The processing module 110 may additionally control the communication module 102 to send/receive information to/from other devices.

In some examples, the processing module 110 may include a pre-programmed chip, such as a very-large-scale integration (VLSI) chip and/or an application specific integrated circuit (ASIC). In such embodiments, the chip may be pre-programmed with control logic in order to control the operation of the LCP 100. By using a pre-programmed chip, the processing module 110 may use less power than other programmable circuits (e.g. general purpose programmable microprocessors) while still being able to maintain basic functionality, thereby potentially increasing the battery life of the LCP 100. In other examples, the processing module 110 may include a programmable microprocessor. Such a programmable microprocessor may allow a user to modify the control logic of the LCP 100 even after implantation, thereby allowing for greater flexibility of the LCP 100 than when using a pre-programmed ASIC. In some examples, the processing module 110 may further include a memory, and the processing module 110 may store information on and read information from the memory. In other examples, the LCP 100 may include a separate memory (not shown) that is in communication with the processing module 110, such that the processing module 110 may read and write information to and from the separate memory.

The battery 112 may provide power to the LCP 100 for its operations. In some examples, the battery 112 may be a non-rechargeable lithium-based battery. In other examples, a non-rechargeable battery may be made from other suitable materials, as desired. Because the LCP 100 is an implantable device, access to the LCP 100 may be limited after implantation. Accordingly, it is desirable to have sufficient battery capacity to deliver therapy over a period of treatment such as days, weeks, months, years or even decades. In some instances, the battery 112 may a rechargeable battery, which may help increase the useable lifespan of the LCP 100. In still other examples, the battery 112 may be some other type of power source (e.g., energy harvest from the body), as desired.

To implant the LCP 100 inside a patient's body, an operator (e.g., a physician, clinician, etc.), may fix the LCP 100 to the cardiac tissue of the patient's heart. To facilitate fixation, the LCP 100 may include one or more anchors 116. The anchor 116 may include any one of a number of fixation or anchoring mechanisms. For example, the anchor 116 may include one or more pins, staples, threads, screws, helix, tines, and/or the like. In some examples, although not shown, the anchor 116 may include threads on its external surface that may run along at least a partial length of the anchor 116. The threads may provide friction between the cardiac tissue and the anchor to help fix the anchor 116 within the cardiac tissue. In other examples, the anchor 116 may include other structures such as barbs, spikes, or the like to facilitate engagement with the surrounding cardiac tissue.

Figure 2:
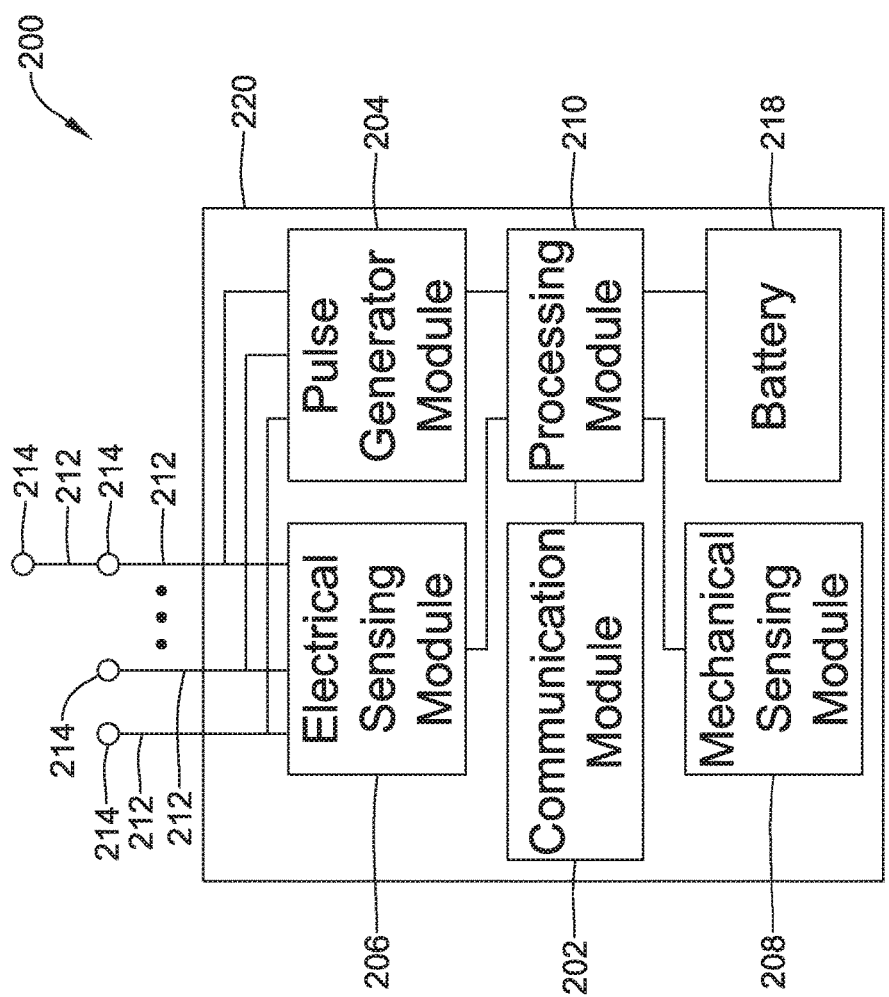
FIG. 2 is a schematic block diagram of another medical device (MD), which may be used in conjunction with an LCP 100 (FIG. 1) in order to detect and/or treat cardiac arrhythmias and other heart conditions.

FIG. 2 depicts an example of another medical device (MD) 200, which may be used in conjunction with an LCP 100 (FIG. 1) in order to detect and/or treat cardiac arrhythmias and other heart conditions. In the example shown, the MD 200 may include a communication module 202, a pulse generator module 204, an electrical sensing module 206, a mechanical sensing module 208, a processing module 210, and a battery 218. Each of these modules may be similar to the modules 102, 104, 106, 108, and 110 of the LCP 100. Additionally, the battery 218 may be similar to the battery 112 of the LCP 100. In some examples, the MD 200 may have a larger volume within the housing 220 than LCP 100. In such examples, the MD 200 may include a larger battery and/or a larger processing module 210 capable of handling more complex operations than the processing module 110 of the LCP 100.

While it is contemplated that the MD 200 may be another leadless device such as shown in FIG. 1, in some instances the MD 200 may include leads such as leads 212. The leads 212 may include electrical wires that conduct electrical signals between the electrodes 214 and one or more modules located within the housing 220. In some cases, the leads 212 may be connected to and extend away from the housing 220 of the MD 200. In some examples, the leads 212 are implanted on, within, or adjacent to a heart of a patient. The leads 212 may contain one or more electrodes 214 positioned at various locations on the leads 212, and in some cases at various distances from the housing 220. Some of the leads 212 may only include a single electrode 214, while other leads 212 may include multiple electrodes 214. Generally, the electrodes 214 are positioned on the leads 212 such that when the leads 212 are implanted within the patient, one or more of the electrodes 214 are positioned to perform a desired function. In some cases, the one or more of the electrodes 214 may be in contact with the patient's cardiac tissue. In some cases, the one or more of the electrodes 214 may be positioned substernally or subcutaneously but adjacent the patient's heart. In some cases, the electrodes 214 may conduct intrinsically generated electrical signals to the leads 212, e.g. signals representative of intrinsic cardiac electrical activity. The leads 212 may, in turn, conduct the received electrical signals to one or more of the modules 202, 204, 206, and 208 of the MD 200. In some cases, the MD 200 may generate electrical stimulation signals, and the leads 212 may conduct the generated electrical stimulation signals to the electrodes 214. The electrodes 214 may then conduct the electrical signals and delivery the signals to the patient's heart (either directly or indirectly).

The mechanical sensing module 208, as with the mechanical sensing module 108, may contain or be electrically connected to one or more sensors, such as accelerometers, blood pressure sensors, heart sound sensors, blood-oxygen sensors, acoustic sensors, ultrasonic sensors and/or other sensors which are configured to measure one or more mechanical/chemical parameters of the heart and/or patient. In some examples, one or more of the sensors may be located on the leads 212, but this is not required. In some examples, one or more of the sensors may be located in the housing 220.

While not required, in some examples, the MD 200 may be an implantable medical device. In such examples, the housing 220 of the MD 200 may be implanted in, for example, a transthoracic region of the patient. The housing 220 may generally include any of a number of known materials that are safe for implantation in a human body and may, when implanted, hermetically seal the various components of the MD 200 from fluids and tissues of the patient's body.

In some cases, the MD 200 may be an implantable cardiac pacemaker (ICP). In this example, the MD 200 may have one or more leads, for example leads 212, which are implanted on or within the patient's heart. The one or more leads 212 may include one or more electrodes 214 that are in contact with cardiac tissue and/or blood of the patient's heart. The MD 200 may be configured to sense intrinsically generated cardiac electrical signals and determine, for example, one or more cardiac arrhythmias based on analysis of the sensed signals. The MD 200 may be configured to deliver CRT, ATP therapy, bradycardia therapy, and/or other therapy types via the leads 212 implanted within the heart or in concert with the LCP by commanding the LCP to pace. In some examples, the MD 200 may additionally be configured provide defibrillation therapy.

In some instances, the MD 200 may be an implantable cardioverter-defibrillator (ICD). In such examples, the MD 200 may include one or more leads implanted within a patient's heart. The MD 200 may also be configured to sense cardiac electrical signals, determine occurrences of tachyarrhythmias based on the sensed signals, and may be configured to deliver defibrillation therapy in response to determining an occurrence of a tachyarrhythmia. In some instances, the MD 200 may be a subcutaneous implantable cardioverter-defibrillator (S-ICD). In examples where the MD 200 is an S-ICD, one of the leads 212 may be a subcutaneously implanted lead. In at least some examples where the MD 200 is an S-ICD, the MD 200 may include only a single lead which is implanted subcutaneously, but this is not required. In some cases, the S-ICD lead may extend subcutaneously from the S-ICD can, around the sternum and may terminate adjacent the interior surface of the sternum.

In some examples, the MD 200 may not be an implantable medical device. Rather, the MD 200 may be a device external to the patient's body, and may include skin-electrodes that are placed on a patient's body. In such examples, the MD 200 may be able to sense surface electrical signals (e.g. cardiac electrical signals that are generated by the heart or electrical signals generated by a device implanted within a patient's body and conducted through the body to the skin). In such examples, the MD 200 may be configured to deliver various types of electrical stimulation therapy, including, for example, defibrillation therapy. The MD 200 may be further configured to deliver electrical stimulation via the LCP by commanding the LCP to deliver the therapy.

Figure 3:
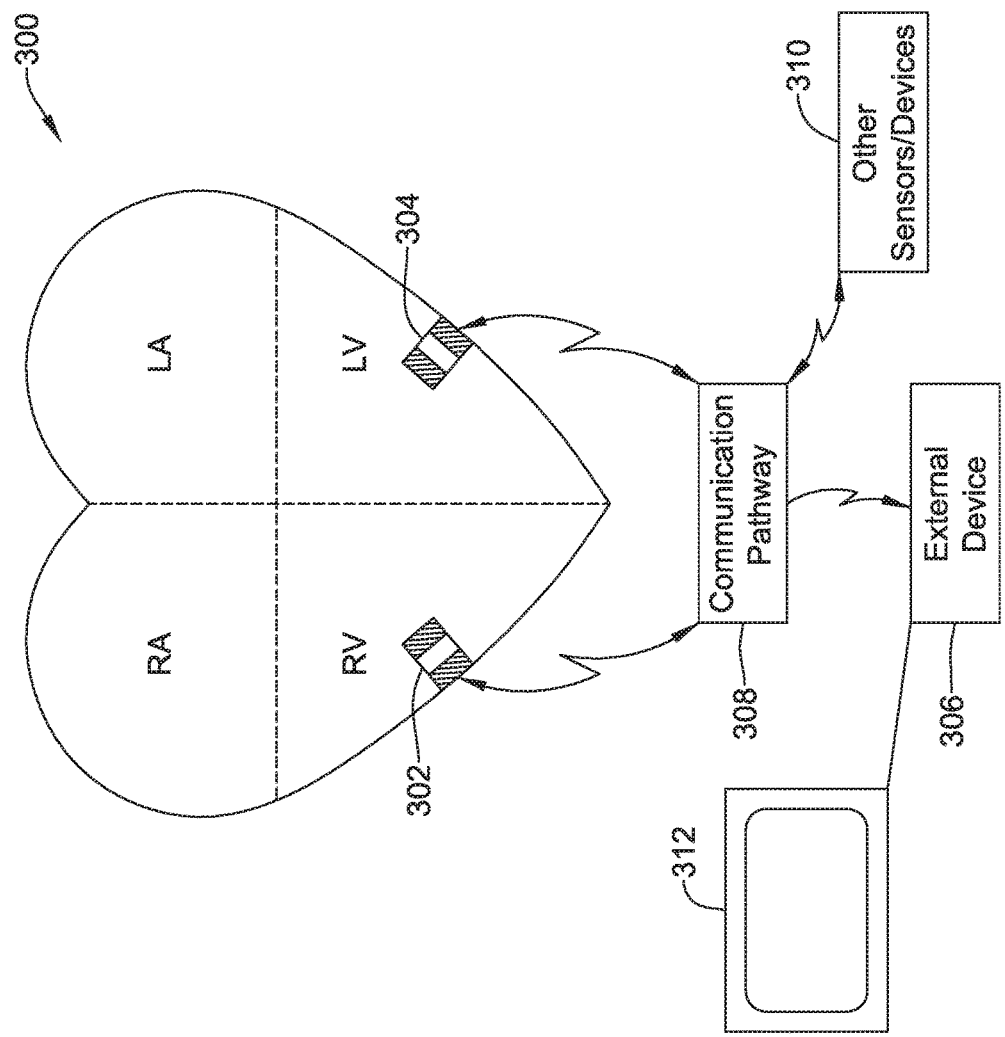
FIG. 3 is a schematic diagram of an exemplary medical system that includes multiple LCPs and/or other devices in communication with one another.

FIG. 3 shows an example medical device system with a communication pathway through which multiple medical devices 302, 304, 306, and/or 310 may communicate. In the example shown, the medical device system 300 may include LCPs 302 and 304, an external medical device 306, and other sensors/devices 310. The external device 306 may be any of the devices described previously with respect to MD 200. In some embodiments, the external device 306 may be provided with or be in communication with a display 312. The display 312 may be a personal computer, tablet computer, smart phone, laptop computer, or other display as desired. In some instances, the display 312 may include input means for receiving an input from a user. For example, the display 312 may also include a keyboard, mouse, actuatable (e.g. pushable) buttons, or a touchscreen display. These are just examples. The other sensors/devices 310 may be any of the devices described previously with respect to the MD 200. In some instances, the other sensors/devices 310 may include a sensor, such as an accelerometer or blood pressure sensor, or the like. In some cases, the other sensors/devices 310 may include an external programmer device that may be used to program one or more devices of the system 300.

Various devices of the system 300 may communicate via a communication pathway 308. For example, the LCPs 302 and/or 304 may sense intrinsic cardiac electrical signals and may communicate such signals to one or more other devices 302/304, 306, and 310 of the system 300 via the communication pathway 308. In one example, one or more of the devices 302/304 may receive such signals and, based on the received signals, determine an occurrence of an arrhythmia. In some cases, the device or devices 302/304 may communicate such determinations to one or more other devices 306 and 310 of the system 300. In some cases, one or more of the devices 302/304, 306, and 310 of the system 300 may take action based on the communicated determination of an arrhythmia, such as by delivering a suitable electrical stimulation to the heart of the patient. In another example, the LCPs 302 and/or 304 may sense indications of blood pressure (e.g. via one or more pressure sensors) and indications of volume (e.g. via an impedance between the electrodes of an LCP or between LCPs via an ultrasound transducer placed within the LCP, or via strain sensors placed on the heart in communication with the LCP). In one example, one or more of the devices 302/304 may receive such signals and, based on the received signals, determine a pressure-volume loop, and in some cases may communicate such information to one or more other devices 302/304, 306, and 310 of the system 300 via the communication pathway 308.

It is contemplated that the communication pathway 308 may communicate using RF signals, inductive coupling, conductive coupling optical signals, acoustic signals, or any other signals suitable for communication. Additionally, in at least some examples, the device communication pathway 308 may comprise multiple signal types. For instance, the other sensors/device 310 may communicate with the external device 306 using a first signal type (e.g. RF communication) but communicate with the LCPs 302/304 using a second signal type (e.g. conducted communication, inductive communication). Further, in some examples, communication between devices may be limited. For instance, as described above, in some examples, the LCPs 302/304 may communicate with the external device 306 only through the other sensors/devices 310, where the LCPs 302/304 send signals to the other sensors/devices 310, and the other sensors/devices 310 relay the received signals to the external device 306.

In some cases, the communication pathway 308 may include conducted communication. Accordingly, devices of the system 300 may have components that allow for such conducted communication. For instance, the devices of the system 300 may be configured to transmit conducted communication signals (e.g. current and/or voltage pulses) into the patient's body via one or more electrodes of a transmitting device, and may receive the conducted communication signals (e.g. pulses) via one or more electrodes of a receiving device. The patient's body may "conduct" the conducted communication signals (e.g. pulses) from the one or more electrodes of the transmitting device to the electrodes of the receiving device in the system 300. In such examples, the delivered conducted communication signals (e.g. pulses) may differ from pacing or other therapy signals. For example, the devices of the system 300 may deliver electrical communication pulses at an amplitude/pulse width that is sub-threshold to the heart. Although, in some cases, the amplitude/pulse width of the delivered electrical communication pulses may be above the capture threshold of the heart, but may be delivered during a refractory period of the heart and/or may be incorporated in or modulated onto a pacing pulse, if desired.

Delivered electrical communication pulses may be modulated in any suitable manner to encode communicated information. In some cases, the communication pulses may be pulse width modulated or amplitude modulated. Alternatively, or in addition, the time between pulses may be modulated to encode desired information. In some cases, conducted communication pulses may be voltage pulses, current pulses, biphasic voltage pulses, biphasic current pulses, or any other suitable electrical pulse as desired.

In some cases, the communication pathway 308 may include inductive communication, and when so provided, the devices of the system 300 may be configured to transmit/receive inductive communication signals.

Figure 4:
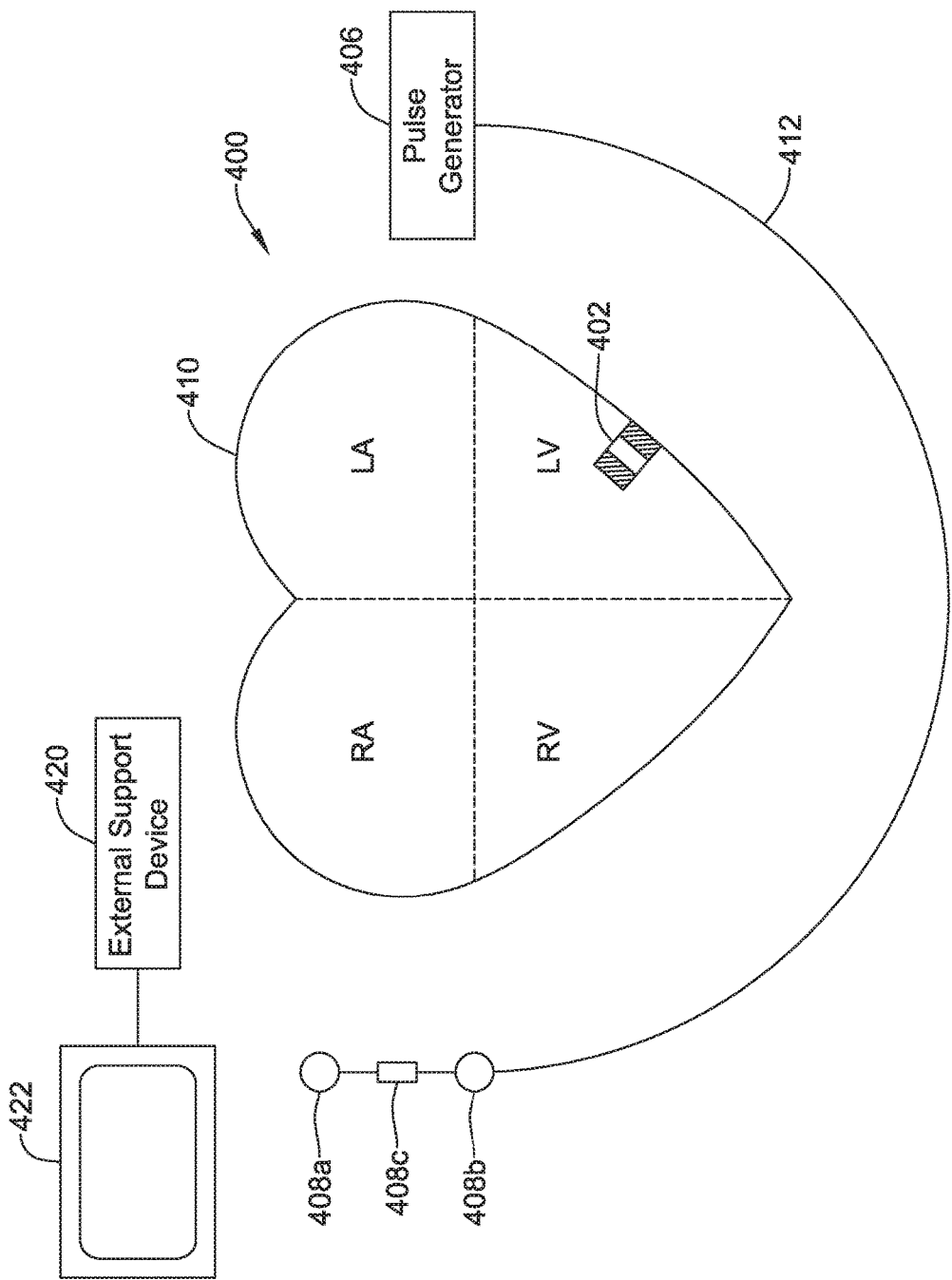
FIG. 4 is a schematic diagram of an exemplary medical system that includes an LCP and another medical device, in accordance with yet another example of the present disclosure.
Figure 5:
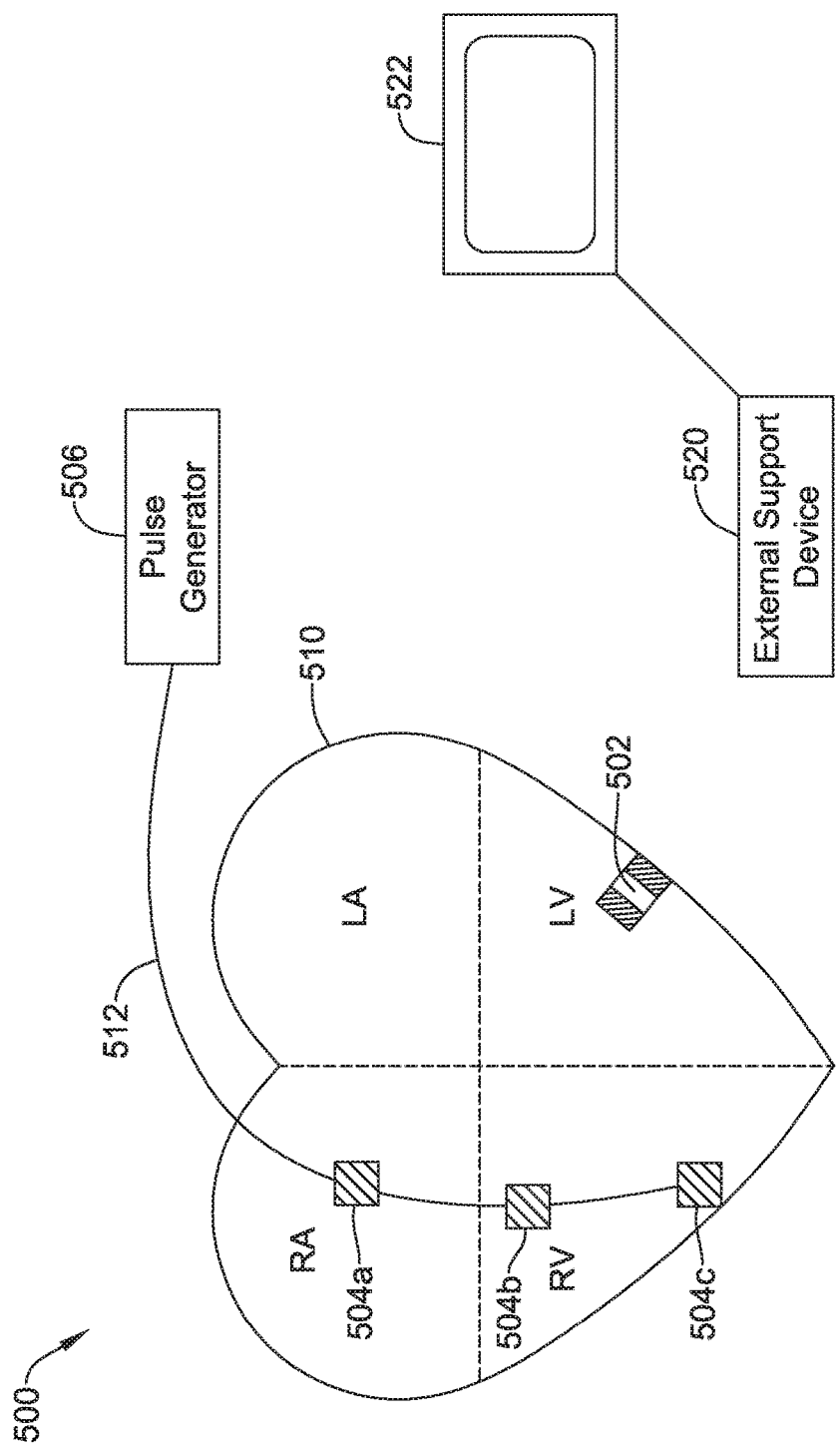
FIG. 5 is a schematic diagram of an exemplary medical system that includes an LCP and another medical device, in accordance with yet another example of the present disclosure.

FIGS. 4 and 5 show illustrative medical device systems that may be configured to operate according to techniques disclosed herein. In FIG. 4, an LCP 402 is shown fixed to the interior of the left ventricle of the heart 410, and a pulse generator 406 is shown coupled to a lead 412 having one or more electrodes 408a, 408b, 408c. In some cases, the pulse generator 406 may be part of a subcutaneous implantable cardioverter-defibrillator (S-ICD), and the one or more electrodes 408a, 408b, 408c may be positioned subcutaneously adjacent the heart. In some cases, the S-ICD lead may extend subcutaneously from the S-ICD can, around the sternum and one or more electrodes 408a, 408b, 408c may be positioned adjacent the interior surface of the sternum. In some cases, the LCP 402 may communicate with the subcutaneous implantable cardioverter-defibrillator (S-ICD).

In some cases, the LCP 402 may be in the right ventricle, right atrium or left atrium of the heart, as desired. In some cases, more than one LCP 402 may be implanted. For example, one LCP may be implanted in the right ventricle and another may be implanted in the right atrium. In another example, one LCP may be implanted in the right ventricle and another may be implanted in the left ventricle. In yet another example, one LCP may be implanted in each of the chambers of the heart.

In FIG. 5, an LCP 502 is shown fixed to the interior of the left ventricle of the heart 510, and a pulse generator 506 is shown coupled to a lead 512 having one or more electrodes 504a, 504b, 504c. In some cases, the pulse generator 506 may be part of an implantable cardiac pacemaker (ICP) and/or an implantable cardioverter-defibrillator (ICD), and the one or more electrodes 504a, 504b, 504c may be positioned in the heart 510. In some cases, the LCP 502 may communicate with the implantable cardiac pacemaker (ICP) and/or an implantable cardioverter-defibrillator (ICD).

The medical device systems 400 and 500 may also include an external support device, such as external support devices 420 and 520. The external support devices 420 and 520 can be used to perform functions such as device identification, device programming and/or transfer of real-time and/or stored data between devices using one or more of the communication techniques described herein. As one example, communication between the external support device 420 and the pulse generator 406 is performed via a wireless mode, and communication between the pulse generator 406 and the LCP 402 is performed via a conducted mode. In some examples, communication between the LCP 402 and the external support device 420 is accomplished by sending communication information through the pulse generator 406. However, in other examples, communication between the LCP 402 and the external support device 420 may be via a communication module. In some embodiments, the external support devices 420, 520 may be provided with or be in communication with a display 422, 522. The display 422, 522 may be a personal computer, tablet computer, smart phone, laptop computer, or other display as desired. In some instances, the display 422, 522 may include input means for receiving an input from a user. For example, the display 422, 522 may also include a keyboard, mouse, actuatable buttons, or be a touchscreen display. These are just examples.

FIGS. 4-5 illustrate two examples of medical device systems that may be configured to operate according to techniques disclosed herein. Other example medical device systems may include additional or different medical devices and/or configurations. For instance, other medical device systems that are suitable to operate according to techniques disclosed herein may include additional LCPs implanted within the heart. Another example medical device system may include a plurality of LCPs without other devices such as the pulse generator 406 or 506, with at least one LCP capable of delivering defibrillation therapy. In yet other examples, the configuration or placement of the medical devices, leads, and/or electrodes may be different from those depicted in FIGS. 4 and 5. Accordingly, it should be recognized that numerous other medical device systems, different from those depicted in FIGS. 4 and 5, may be operated in accordance with techniques disclosed herein. As such, the examples shown in FIGS. 4 and 5 should not be viewed as limiting in any way.

During a heartbeat, the left ventricle twists in systole, storing potential energy, and untwists (e.g., recoils) in diastole, releasing the stored energy. The twist aids in left ventricular ejection and the untwist aids in relaxation and ventricular filling. Looking from the apex, counterclockwise rotation of the left ventricle is expressed with positive values and clockwise rotation is expressed with negative values, generally in units of degrees. A heart has an apex and a base opposite the apex. The apex is located at the lower superficial part of the heart, typically at the lower tip of the left ventricle. The base is along the upper part of heart, and primarily involves the left atrium, part of the right atrium, and portions of the great vessels. In a normal heart, the base rotates clockwise during systole and the apex rotates counterclockwise, producing a wringing motion. The difference in turning angle between the base and the apex is called the net twist angle or net torsion angle, often expressed in degrees. A left ventricle ejection fraction of 55 percent or higher is considered normal. A left ventricle ejection fraction of 50 percent or lower is considered reduced. An ejection fraction between 50 and 55 percent may be considered to be a "borderline" range. A patient in heart failure may have an ejection fraction in the range of 30 percent. Without twisting, the ejection fraction of the left ventricle may be in the range of 15 to 20 percent. Understanding the ventricular twist of a patient's heat may facilitate optimization of treatment in a patient with an implantable medical device such as any of those described herein. In this disclosure, a gyroscope is used to monitor ventricular twisting.

Figure 6:
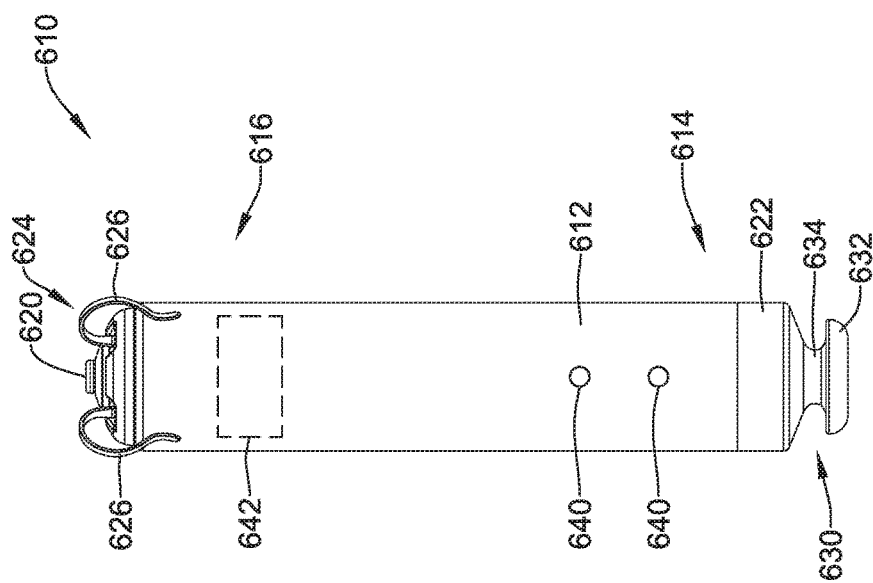
FIG. 6 is a side view of an illustrative implantable leadless cardiac pacing device.

FIG. 6 is a side view of an illustrative implantable leadless cardiac pacemaker (LCP) 610. The LCP 610 may be similar in form and function to the LCP 100 described above. The LCP 610 may include any of the modules and/or structural features described above with respect to the LCP 100. The LCP 610 may include a shell or housing 612 having a proximal end 614 and a distal end 616. The illustrative LCP 610 includes a first electrode 620 secured relative to the housing 612 and positioned adjacent to the distal end 616 of the housing 612, and a second electrode 622 secured relative to the housing 612 and positioned adjacent to the proximal end 614 of the housing 612. In some cases, the housing 612 may include a conductive material and may be insulated along a portion of its length. A section along the proximal end 614 may be free of insulation so as to define the second electrode 622. The electrodes 620, 622 may be sensing and/or pacing electrodes to provide electro-therapy and/or sensing capabilities. The first electrode 620 may be capable of being positioned against or may otherwise contact the cardiac tissue of the heart while the second electrode 622 may be spaced away from the first electrode 620. The first and/or second electrodes 620, 622 may be exposed to the environment outside the housing 612 (e.g. to blood and/or tissue).

In some cases, the LCP 610 may include a pulse generator (e.g., electrical circuitry) and a power source (e.g., a battery) within the housing 612 to provide electrical signals to the electrodes 620, 622 to control the pacing/sensing electrodes 620, 622. While not explicitly shown, the LCP 610 may also include a communications module, an electrical sensing module, a mechanical sensing module, and/or a processing module, and the associated circuitry, similar in form and function to the modules 102, 106, 108, 110 described above. The various modules and electrical circuitry may be disposed within the housing 612.

In the example shown, the LCP 610 includes a fixation mechanism 624 proximate the distal end 616 of the housing 612. The fixation mechanism 624 is configured to attach the LCP 610 to a wall of the heart H, or otherwise anchor the LCP 610 to the anatomy of the patient. As shown in FIG. 6, in some instances, the fixation mechanism 624 may include one or more, or a plurality of hooks or tines 626 anchored into the cardiac tissue of the heart H to attach the LCP 610 to a tissue wall. In other instances, the fixation mechanism 624 may include one or more, or a plurality of passive tines, configured to entangle with trabeculae within the chamber of the heart H and/or a helical fixation anchor configured to be screwed into a tissue wall to anchor the LCP 610 to the heart H. These are just examples.

The LCP 610 may further include a docking member 630 proximate the proximal end 614 of the housing 612. The docking member 630 may be configured to facilitate delivery and/or retrieval of the LCP 610. For example, the docking member 630 may extend from the proximal end 614 of the housing 612 along a longitudinal axis of the housing 612. The docking member 630 may include a head portion 632 and a neck portion 634 extending between the housing 612 and the head portion 632. The head portion 632 may be an enlarged portion relative to the neck portion 634. For example, the head portion 632 may have a radial dimension from the longitudinal axis of the LCP 610 that is greater than a radial dimension of the neck portion 634 from the longitudinal axis of the LCP 610. In some cases, the docking member 630 may further include a tether retention structure (not explicitly shown) extending from or recessed within the head portion 632. The tether retention structure may define an opening configured to receive a tether or other anchoring mechanism therethrough. The retention structure may take any shape that provides an enclosed perimeter surrounding the opening such that a tether may be securably and releasably passed (e.g. looped) through the opening. In some cases, the retention structure may extend though the head portion 632, along the neck portion 634, and to or into the proximal end 614 of the housing 612. The docking member 630 may be configured to facilitate delivery of the LCP 610 to the intracardiac site and/or retrieval of the LCP 610 from the intracardiac site. While this describes one example docking member 630, it is contemplated that the docking member 630, when provided, can have any suitable configuration.

In some cases, the LCP 610 may include one or more pressure sensors 640 coupled to or formed within the housing 612 such that the pressure sensor(s) is exposed to and/or otherwise operationally coupled with the environment outside the housing 612 to measure blood pressure within the heart. In some cases, the pressure sensor 640 may be coupled to an exterior surface of the housing 612. In other cases, the pressures sensor 640 may be positioned within the housing 612 with a pressure acting on the housing and/or a port on the housing 612 to affect the pressure sensor 640. If the LCP 610 is placed in the left ventricle, the pressure sensor(s) 640 may measure the pressure within the left ventricle. If the LCP 610 is placed in another portion of the heart (such as one of the atriums or the right ventricle), the pressures sensor(s) may measure the pressure within that portion of the heart.

The pressure sensor(s) 640 may include a MEMS device, such as a MEMS device with a capacitive diaphragm or a piezoresistive diaphragm, a piezoelectric sensor, a condenser, a micromanometer, or any other suitable sensor adapted for measuring cardiac pressure. The pressures sensor(s) 640 may be part of a mechanical sensing module described herein. It is contemplated that the pressure measurements obtained from the pressures sensor(s) 640 may be used to generate a pressure curve over cardiac cycles. Frequent pressure monitoring may be beneficial for management of heart failure patients. Frequent pressure monitoring may also be useful for patients with chronic heart disease, hypertension, regurgitation, valve issues, and other issues. It is further contemplated that the pressure sensor(s) 640 may be used for monitoring respiration and associated diseases (e.g., chronic obstructive pulmonary disease (COPD), etc.). The pressure readings may be taken in combination with a cardiac chamber volume measurement such as impedance measurements (e.g. the impedance between electrodes 620 and 622) to generate a pressure-impedance loop for one or more cardiac cycles. The impedance may be a surrogate for chamber volume, and thus the pressure-impedance loop may be representative of a pressure-volume loop for a chamber of the heart H.

The LCP 610 may further include a gyroscope 642. The gyroscope 642 may be positioned within the housing 612 along with the processing module, battery, and/or other modules. It is contemplated that the gyroscope 642 may be 1-axis, a 2-axis, or a 3-axis gyroscope, as desired. The gyroscope 642 may be selected to balance power consumption, physical size and usage. For example, a 3-axis gyroscope may provide the most accurate data regarding the movement of the left ventricle, but may also consume the most power. In order to manage power consumption, the number of axes may be limited. Alternatively, or additionally, to further manage power consumption, the gyroscope 642 may be enabled for only certain short periods of certain heart cycle (e.g., triggered by a heart sound trigger and enabled for only a short time period, only for 1 of every N cycles, etc.) The pressure sensor 640 and/or electrodes 620, 622 may provide information to the circuitry regarding the cardiac cycle to allow the gyroscope 642 to be selectively activated at useful times, such as during a maximum contraction of the heart (at max positive dP/dt) and/or during max filling (at max negative dP/dt). In some cases, the gyroscope 642 may continuously acquire data related to the movement of the heart, at least for a period of time.

In some embodiments, the gyroscope 642 may be a stand-alone gyroscope. An illustrative gyroscope suitable for use inside the housing 612 of the LCP 610 is the ADXRS290 manufactured by Analog Device™. The ADXRS290 is a MEMS device which has an approximate size of 5×5×1.2 millimeters. In other embodiments, the gyroscope 642 may be integrated with an accelerometer to provide a full inertial measurement unit (IMU). For example, the inclusion of a 3-axis accelerometer with the gyroscope 642 may together provide six degrees of freedom. An illustrative device including a 3-axis gyro and accelerometer is the MC7030 iGyro™ manufactured by mCube™. The MC7030 iGyro™ also includes a 3-axis magnetometer sensor (in addition to the 3-axis accelerometer and the 3-axis gyroscope) giving the device nine degrees of freedom. These are just example devices that are suitable for use in LCP 610. However, it is contemplated that any suitable gyroscope may be used in or with the LCP 610.

It may be desirable to position the gyroscope 642 as close to the left ventricle apex as possible, although a location near the apex on the free-wall may be sufficient. In some cases, it may be desirable to use magnetic resonance imaging (MM) or ultrasound to determine the optimal location within the heart for measuring cardiac twist. The optimum location for measuring cardiac twist may be different from the optimum location for implantation of the LCP 610 for performing cardiac pacing. In such an instance, it may be desirable to provide the gyroscope 642 as a separate component from the LCP 610 or as a tethered system that can be attached to the LCP 610 (see FIG. 7B).

Figure 7A:
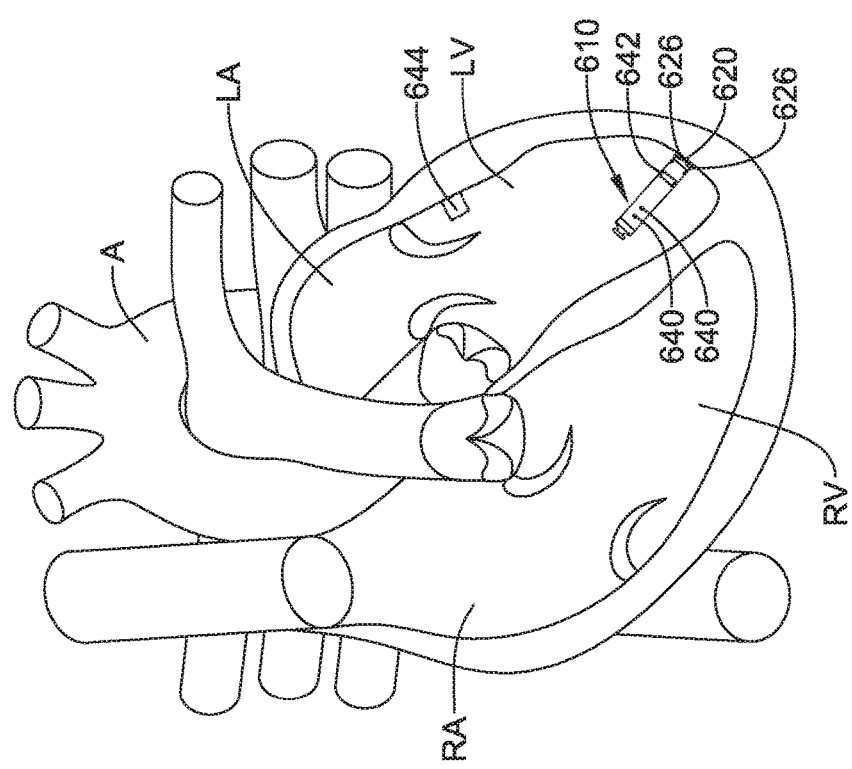
FIG. 7A is a partial cross-sectional plan view of an example leadless cardiac pacing device implanted within a heart during ventricular filling.

FIG. 7A is a partial cross-sectional plan view of the example leadless cardiac pacing device 610 implanted within a left ventricle LV of the heart H during ventricular filling. The right ventricle RV, right atrium RA, left atrium LA, and aorta A are also illustrated. As detailed above, the LCP 610 may include the gyroscope 642 disposed within the housing 612 of the LCP 610. In some cases, a second gyroscope 644 may also be provided. The second gyroscope 644 may be provided as a stand-alone device or as a part of an additional LCP device, as desired. When a second gyroscope is provided, it may be desirable for the first gyroscope 642 to be positioned near the apex of the heart and the second gyroscope 644 to be positioned near the base of the left ventricle, such as shown in FIG. 7A. This may allow two different twist directions to be more readily captured. The second gyroscope 644 may be in wireless communication with the LCP 610 and/or an external device.

Figure 7B:
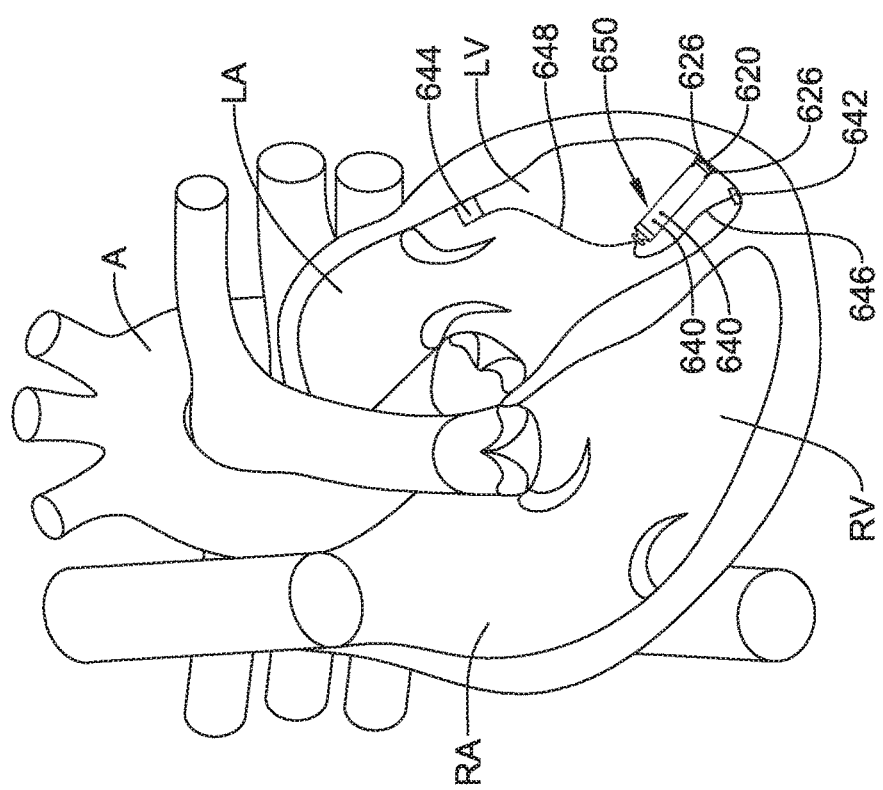
FIG. 7B is a partial cross-sectional plan view of another example leadless cardiac pacing device implanted within a heart during ventricular filling.

FIG. 7B is another partial cross-sectional plan view of another illustrative leadless cardiac pacing device 650 implanted within a left ventricle LV of the heart H during ventricular filling. The right ventricle RV, right atrium RA, left atrium LA, and aorta A are also illustrated. The illustrative LCP 650 may include the gyroscope 642 provided as a modular tethered system. The gyroscope 642 may be electrically connected to the LCP 650 through a tail or tether 646. This may allow both the gyroscope 642 and the LCP 650 to be positioned in their optimum locations. In some embodiments, a second gyroscope 644 may be provided adjacent to the base of the left ventricle as a stand-alone device or electrically connected to the LCP 650 through a tail or tether 648. In some embodiments, the second gyroscope 644 may be the only gyroscope. In other words, the first gyroscope 642, positioned at the apex, may not be present.

It is also contemplated that the LCP 650 may itself include a gyroscope, similar to LCP 610 of FIG. 7A, and may include a second gyroscope may be electrically connected via a tether (such as the tether 648 illustrated in FIG. 7B). In another example, a single gyroscope may be provided as a stand-alone system in any desired location. The stand-alone gyroscope may be in wired or wireless communication with an implanted LCP or an external device.

During placement of the gyroscope 642 (either as a part of the LCP 610 or as a stand-alone system), a pressure sensor in the delivery catheter or LCP 610 may be used to correlate pressure and twist. For example, the peak angle of rotation of the twist during systole may generally occur at the same time as the peak pressure (max dP/dt). Thus, in some cases, the gyroscope 642 may be enabled during this time. Also, certain cardiac conditions may be detected by determine the relative measures of pressure and twist. For example, it may be beneficial to determine when max dP/dt is down, whether max twist angle, max twist speed and or other twist parameter are also down or not. In addition, it may be desirable to coordinate torsional measurements with other factors, including, but not limited to: time of day, an accelerometer in the LCP 610 (or other device such an S-ICD, ICM, etc.), a respiratory or cardiac signal (e.g. via transthoracic impedance). In some cases, the gyroscope 642 may be configured to obtain measurements in response to an external device, such as, but not limited to a handheld patient unit or external programmer.

Figure 8:
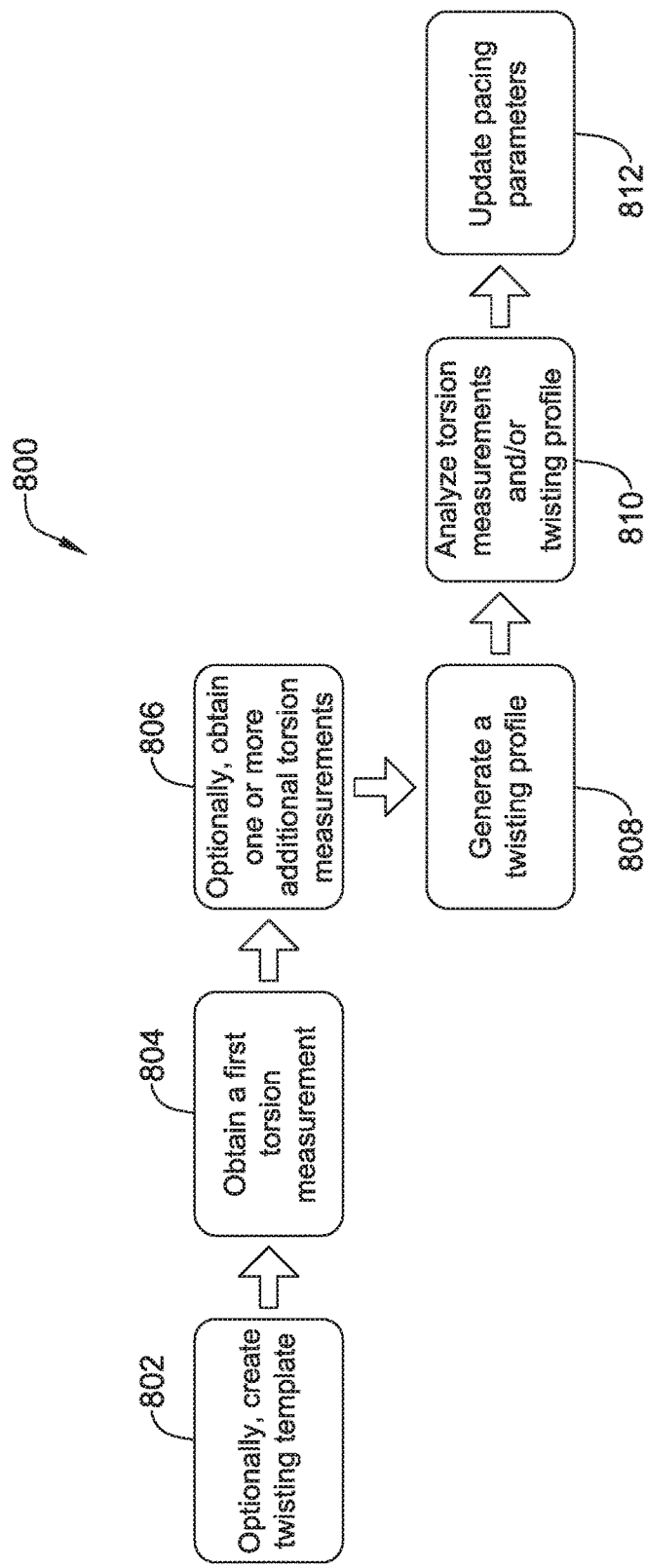
FIG. 8 is a flow diagram of an illustrative method for generating a twisting profile for a ventricle of a human heart.

Normal hearts (e.g., well-functioning hearts) may have a "typical" twist (e.g. degree of rotation, twist vector, and/or speed of rotation) associated with each cardiac cycle. The twist vector may be the axis normal to the plane of the twist. The angular motion (e.g. twist or torsion of the left ventricle), as measured by the gyroscope 642, may be used to help identify a suitable pacing site and/or suitable timing for cardiac resynchronization therapy (CRT). FIG. 8 is a flow chart of an illustrative method 800 for generating a twisting profile of the left ventricle of a heart from data obtained from an implanted LCP with a gyroscope such LCP 610. While the method is described using an LCP having a gyroscope within the housing, it is contemplated that other devices and/or combinations of devices may be used. For example, a second gyroscope (stand-alone or in combination with an LCP) may be used to collect data from a different location in the heart. As described above, the LCP may include a processing module that includes control circuitry configured to control the operation of the LCP. In some instances, the processing module may include separate circuits for therapy delivery, torsion sensing, hemodynamic (e.g. pressure) sensing, and/or volume sensing, although this is not required. It is contemplated that the processing module may further include an additional circuit or algorithm for generating a twisting profile that may be configured to convert the data obtained from one or more gyroscopes into a twist profile. As used herein, a twisting profile may be a temporal progression or point in time of the angular velocity including a single torsion measurement (e.g. max twist angle, max twist speed, etc.), a plurality of torsion measurements obtained over a single cardiac cycle, an average of torsion measurements (either single data points or multiple data points in the same cardiac cycle) obtained over a plurality of cardiac cycles, and/or any other suitable measurement or combination of measurements. In some cases, the twisting profile may be based on any signal characteristic obtained from the gyroscope signals including, but not limited to, based on amplitude, frequency, temporal association, morphology, etc. It is further comtemplated that other characteristics may form the twisting profile, or be extracted from the twisting profile, including, but not limited to the maximum amplitude reached during a cardiac beat, the timing of the maximum amplitude within the beat, the area under curve for the portion of the curve where twist occurs in the abnormal direction, etc.

As shown at block 802, an optional twisting template using one or more torsion measurements (e.g., degree of rotation and/or speed of rotation) may be generated. The twisting template may be generated at the time of implantation (sometimes using MRI, ultrasound and/or the gyroscope) or at a time point (or plurality of time points) previous to a current measurements. The twist template may characterize the typical twisting action of the patient's heart when the heart is operating in a healthy manner. In some instances, the twist (e.g., torsion) may be measured for both sensed beats and paced beats, and different twisting templates may be generated for each type of beat. In many cases, and because of the different conduction, the twisting action and thus the twisting template is expected to be different for sensed beats (i.e. intrinsic beats) versus paced beats.

The twist template may be updated at regular, or predefined intervals or based on a detected condition changes (e.g., exercise, heart failure (HF) status, posture, therapy modification, cardiac status, pacing status, etc.), as desired. In some cases, a different twist template may be created, stored and updated for each of a number of predetermined conditions. For example, a twist template may be created, stored and updated for each of several different postures (e.g. lying down, sitting, walking, etc.) Then, during subsequent operation, the LCP may sense a current posture and use the corresponding twist template for comparison with a currently sensed twisting profile.

As shown at block 804, the processing module and/or any other circuits of one or more LCPs (and/or other implantable devices) may obtain a torsion measurement using the gyro. The torsion measurements may include, for example, max twist angle, max twist speed, max twist acceleration, twist angle sampled over a time period, twist speed sampled over a time period, twist acceleration sampled over a time period, a twist vector indicating an average, max, min or other twist direction, twist direction sampled over a time period, and/or any other suitable torsion parameter.

In some instances, the torsion measurement may be made at a first time or during a first time period during a cardiac cycle. The first time or first time period may be triggered using an R wave or an S1 heart sound, although this is not required. In other instances, the first time or first time period may be triggered using the peak pressure (max dP/dt). The data may be stored in a memory of the LCP. In some instances, the data may be stored in a table. In some cases, the data may be transmitted to a remote device, such as another LCP, an S-ICD device, or an external device. The processing module may optionally obtain one or more additional torsion measurements at different times during the same cardiac cycle, as shown at block 806. The one or more torsion measurements may be analyzed to generate a twisting profile, as shown at block 808. In the case where more than one gyroscope has been provided, multiple measurements may be taken and used for analyzing same cardiac cycle. For example, torsional measurements for the apex, base, and/or other location may be taken and used to generate the twisting profile.

In some instances, the processing module may include circuitry to analyze the data and generate the twisting profile. In other instances, the LCP circuitry may be configured to wirelessly transmit the torsion measurements to a remote or external device, such as, but not limited to, any of the medical or external devices described above. The LCP may communicate with the remote or external device via radiofrequency (RF) signals, inductive coupling, optical signals, acoustic signals, conducted communication signals, and/or any other signals suitable for communication. The remote or external device may then analyze the torsional measurements and generate the twisting profile. In some cases, the generated twisting profile may be communicated back to the LCP.

It is contemplated that torsion measurements obtained over a plurality (e.g. two or more, five or more, ten or more) of cardiac cycles may be averaged to generate a twisting profile. For example, the LCP circuitry may be configured to record or sample torsion or twisting at the same (or similar) time points in each of a series of cardiac cycles such that the first torsion measurement from a first cardiac cycle can be averaged with the corresponding first torsion measurement from any number of subsequent (or preceding) cardiac cycles. Any other torsional measurements may be similarly average. Averaging the data over a plurality of cardiac cycles may reduce the noise and provide a more robust representation of the twisting profile. In some cases, the averaging may be weighted so that more current torsion measurements are weighted higher than older torsion measurements.

As shown at block 810, the torsion measurements and/or twisting profile may be analyzed (e.g., in the internal circuitry of the LCP, the circuitry of another device, and/or a physician's analysis) to determine how the heart is currently functioning. In some cases, the twisting profile may be compared to a twisting template, although this is not required. In some cases, a net LV twist below a threshold value may indicate that pacing and/or other therapy can be further optimized. In other instances, a twist velocity below a threshold velocity may indicate that pacing and/or other therapy can be further optimized. In some cases, features extracted from the twisting profile (e.g., twist rate of change) may be used to make treatment decisions or to provide diagnostic information. To save on power, the torsion measurements and/or twisting profile may be based on one axis of a gyroscope (e.g., the perpendicular plane to the normal vector from the LV apex), although more than one axis may be used when desired. The twisting profile may be updated at regular, or predefined intervals.

If the pacing and/or other therapy can be further optimized, the LCP circuitry may be configured adjust pacing and/or other parameters of the LCP, as shown at block 812. For example, the AV delay and/or VV delay may be adjusted to help improve the twist of the heart. In some cases, the voltage and/or pulse width required to reliably depolarize (capture) the heart may be adjusted. Alternatively, or additionally, the level of fusion may be manipulated by either pacing a marginally earlier or delaying a pace to wait for an intrinsic beat. In some cases, the physical location of the pacing electrode of the LCP may be changed to increase the twist of the heart. It is contemplated that the torsion measurements and/or twisting profile may be used for additional analysis of the cardiac function, as desired.

Figure 9:
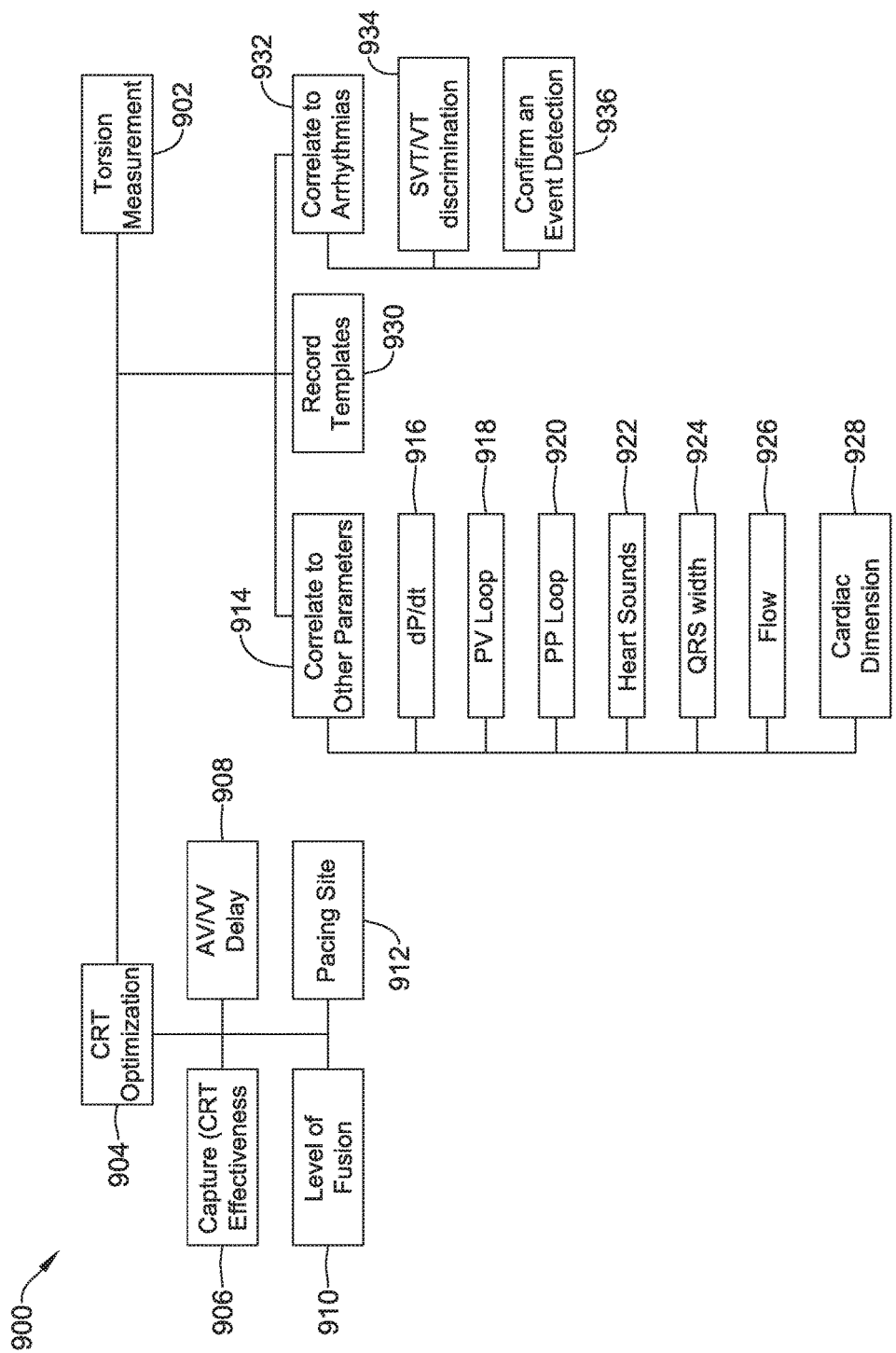
FIG. 9 is a diagram showing illustrative uses of torsion measurements for the ventricle.

FIG. 9 is a diagram 900 illustrating some, but not all, potential uses of one more torsion measurements 902 (e.g. degree of rotation, speed of rotation, and/or features that can be extracted from the torsion measurements, such as, but not limited to rate of change).

The torsion measurements 902 may be obtained at a single time in the cardiac cycle (e.g., peak torsion) or a plurality of sample times during the same cardiac cycle. In some cases, the torsion measurements may be obtained over one or more cardiac cycles (either using a single time or plurality of sample times in the same cardiac cycle) at similar times, and the measurements averaged, as described above. A single torsion measurement, a plurality of torsion measurements, a single point averaged over one or more cardiac cycles, and/or a plurality of points each averaged over one or more cardiac cycles may individually or together form a twisting profile of the heart.

As described above, the torsion measurements may be used for treatment optimization, as shown at block 904. Some pacing parameters that may be manipulated include, but are not limited to capture (CRT effectiveness) 906, AV and/or VV delay 908, level of fusion 910, and/or the pacing site 912. In some instances, the LCP circuitry may be configured to compare or correlate the torsion measurements and/or twisting profile with other parameters, as shown at block 914. In some cases, this correlation may be performed by other external devices described herein, or the LCP itself. Some illustrative parameters that the torsion measurements and/or twisting profile may be compared or correlated with may include, but are not limited to, dP/dt (change in pressure with respect to time) 916, pressure-volume (PV) loops 918, volume-volume (VV) loops 920, heart sounds 922, an ECG attribute (e.g., QRS signal width) 924, blood flow 926, and/or cardiac dimensions (chamber volume) 928. Other parameters may include, but are not limited to cardiovascular pressure (e.g., ventricular pressure), heart sounds, impedance, cardiac shorting (using a doubly integrated acceleration signal in combination with a twist vector parameter), and/or respiration. The correlation between torsion measurements and/or twisting profile and other parameters may provide the LCP and/or physician with further insight regarding the mechanical performance of the heart and/or facilitate the tracking of various parameters over time. It is further contemplated that pressure or other parameters may be used to adjust pacing and/or other therapy to achieve a desired or optimal angular profile for a patient.

As noted above, the torsion measurements 902 may be used to generate twisting templates that correspond to each of a plurality of different states or conditions (e.g., activity level, HF status, posture, respiration rate, heart rate, etc.) that the patient may be in, as shown at block 930. For example, a twist template may be created, stored and updated for each of several different postures (e.g. lying down, sitting, walking, etc.) Then, during subsequent operation, the LCP may sense a current posture and use the corresponding twist template for comparison with a currently sensed twisting profile.

Additionally, or alternatively, the torsion measurements may be used to facilitate rhythm discrimination. For example, as shown at block 932, the torsion measurements and/or twisting profile may be correlated to different arrhythmias. When the heart rhythm is abnormal, the twisting profile is also expected to be abnormal. In some cases, the twist angle and/or early diastolic twisting may be correlated to a particular arrhythmias type. In some cases, the torsion measurements may be correlated to certain physiological variable such as preload, afterload, contractility, etc. Increased preload can be indicated by an increased peak twist angle and a decreased peak twist velocity. Increased afterload can be indicated by a decreased peak twist angle and a decreased peak twist velocity. An increased contractility can be indicated by an increased peak twist angle and increased peak twist velocity. These and other physiological variables can depending on the type of arrhythmia, and thus can be used to discriminate between types of arrhythmias. In one example, a marker for ventricular tachycardia (VT) may be a substantial drop in afterload relative to a supraventricular tachycardia (SVT), as shown at block 934.

In some cases, the torsion measurements and/or twisting profiles may be used to help confirm an event detection by the LCP and/or an external device such as an SICD or remote programmer, as shown at block 936. For example, the torsion measurements and/or twisting profiles may supplement an LCP's or S-ICD's rhythm discrimination algorithm by confirming an initial detection by other means (e.g. by ECG signals). In some cases, the confirmation of an event may result in the delivery or adjustment of a therapy delivered by the LCP and/S-ICD. For example, the LCP and/or S-ICD may deliver an ATP therapy when one or more twisting parameters indicate a tachyarrhythmia that is treatable with ATP therapy.

Figure 10:
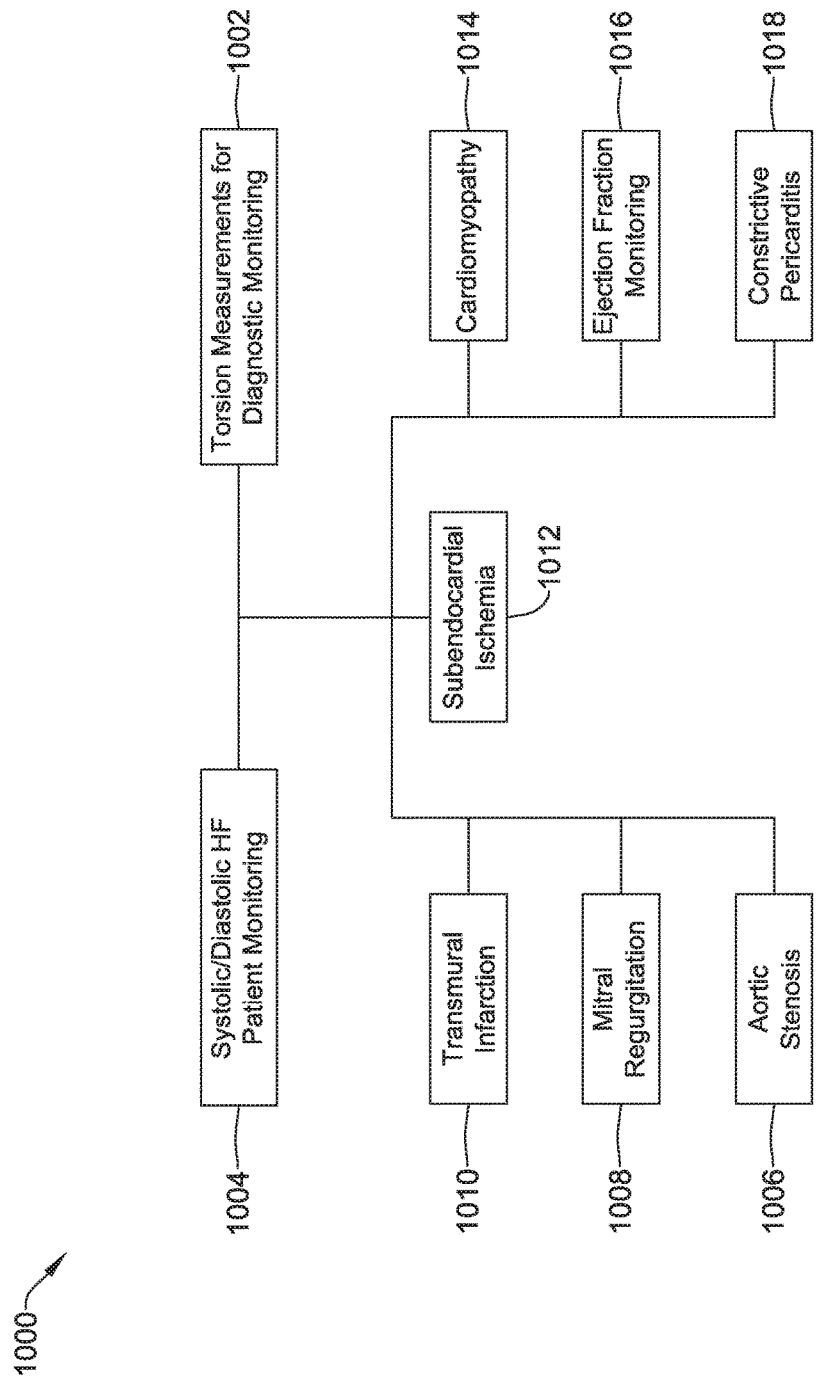
FIG. 10 is another diagram showing illustrative uses of torsion measurements for the ventricle.

In some cases, the torsion measurements and/or twisting profile may be used for diagnostic monitoring of acute and/or chronic conditions. The torsion measurements and/or twisting profile may be combined with other diagnostic parameters such as pressure, chamber volume, etc. to perform the diagnostic monitoring. FIG. 10 is a diagram 1000 illustrating some, but not all, potential uses of one more torsion measurements 1002 (e.g. degree of rotation, speed of rotation, and/or features that can be extracted from a plot of the torsion measurements, such as, but not limited to rate of change) in diagnostic monitoring. In a first example, the torsion measurements and/or twisting profile may be used to monitor systolic and/or diastolic heart failure in patients, as shown at block 1004. The recoil rate (e.g., untwisting velocity) is inversely related to the time constant of LV pressure decay. As such, the recoil rate may be used in monitoring diastolic dysfunction. In some cases, the recoil rate may be a target metric for optimization. For example, when a patient is sleeping, the recoil rate may be optimized for relaxation. In diastolic heart failure, the twist angle may remain neutral or increase and the peak twist velocity may remain neutral or decrease relative to normal. In some cases, the recoil rate and QRS width may be combined to provide a measure of dyssynchrony.

The maximum twisting rate may be similar to the maximum dP/dt and can be used for the monitoring of patients' systolic function. In systolic heart failure, the peak twist angle as well as the peak twist velocity may decrease relative to normal. Further, LV twisting and untwisting rates are reduced in patients with systolic dysfunction and depressed ejection fraction, but not in those with diastolic dysfunction and preserved ejection fraction.

In another example, the torsion measurements and/or twisting profile may be used to monitor aortic stenosis, as shown at block 1006. When aortic stenosis occurs, the peak twist angle may remain neutral or increase and the peak twist velocity may decrease relative to normal.

In another example, the torsion measurements and/or twisting profile may be used to monitor mitral regurgitation, as shown at block 1008. When mitral regurgitation occurs, the peak twist angle may decrease and the peak twist velocity may decrease relative to normal.

In another example, the torsion measurements and/or twisting profile may be used to monitor transmural infarction, as shown at block 1010. When transmural infarction occurs, the peak twist angle may decrease and the peak twist velocity may decrease relative to normal.

In another example, the torsion measurements and/or twisting profile may be used to monitor subendocardial ischemia, as shown at block 1012. When subendocardial ischemia occurs, the peak twist angle may remain neutral and the peak twist velocity may remain neutral or decrease relative to normal.

In another example, the torsion measurements and/or twisting profile may be used to monitor various types of cardiomyopathy, as shown at block 1014. When dilated cardiomyopathy occurs, the peak twist angle may decrease and the peak twist velocity may decrease relative to normal. When hypertrophic cardiomyopathy occurs, the peak twist angle may remain neutral or increase and the peak twist velocity may decrease relative to normal. Patients with hypertrophic cardiomyopathy (HC) show increased peak LV twist, onset of torsion recoil closer to aortic valve closure (e.g., reduction in time between S2 and recoil onset), and delayed peak untwist velocity. When restrictive cardiomyopathy occurs, the peak twist angle may remain neutral or increase and the peak twist velocity may remain neutral relative to normal.

In another example, the torsion measurements and/or twisting profile may be used to monitor constrictive pericarditis, as shown at block 1018. When constrictive pericarditis occurs, the peak twist angle may decrease and the peak twist velocity may decrease relative to normal. These illustrative cardiac diseases are not intended to be inclusive of all of the diseases and/or conditions that can be monitored using torsion measurements and/or twisting profiles. Subendocardial dysfunction can appear with other diseases as well.

It is further contemplated that the torsion measurements and/or twisting profiles may be used to monitor ejection fraction, as shown at block 1016. As described herein, the twist aids in LV ejections and accounts for a large portion of the volume of blood ejected. An abnormal or substandard twist may be associated with an inadequate ejection fraction. As compared with myocardial infarction (MI) patients, heart failure patients present an even more pronounced impairment of LV mechanics, irrespective of the HF etiology as a result of reduction of both LV basal and apical rotation. In some cases, the peak LV twist angle may have a linear relationship with the left ventricle ejection fraction. Thus, the gyroscope measurements may be able to calculate the ejection fraction based on the peak LV twist angle. Therapy may be changed accordingly.

Those skilled in the art will recognize that the present disclosure may be manifested in a variety of forms other than the specific examples described and contemplated herein. For instance, as described herein, various examples include one or more modules described as performing various functions. However, other examples may include additional modules that split the described functions up over more modules than that described herein. Additionally, other examples may consolidate the described functions into fewer modules. Accordingly, departure in form and detail may be made without departing from the scope and spirit of the present disclosure as described in the appended claims.

What is claimed is:

1. A leadless cardiac pacemaker (LCP) configured to sense cardiac activity and to pace a patient's heart, the LCP comprising:
   a housing;
   an electrode secured relative to the housing and exposed to an environment outside of the housing;
   a gyroscope disposed relative to the housing;
   circuitry in the housing in communication with the electrode and the gyroscope, the circuitry configured to generate a twisting profile over one or more cardiac cycles based at least in part on data obtained from the gyroscope;
   wherein the circuitry is further configured to:
      update one or more pacing parameters of the LCP based at least in part on the twisting profile; and
      pace the patient's heart with the electrode using one or more of the updated pacing parameters.

2. The LCP of claim 1, wherein the circuitry is configured to update the twisting profile at a predefined regular interval.

3. The LCP of claim 1, wherein the circuitry is configured to update the twisting profile in response to a detected condition change.

4. The LCP of claim 1, wherein the detected condition change corresponds to one of exercise, heart failure status, therapy modification, cardiac status, pacing status, or posture.

5. The LCP of claim 1, wherein updating the one or more pacing parameters of the LCP comprises adjusting an AV delay.

6. The LCP of claim 1, wherein updating the one or more pacing parameters of the LCP comprises adjusting a VV delay.

7. The LCP of claim 1, wherein the circuitry is further configured to compare the twisting profile to an additional parameter to determine if the twisting profile is abnormal.

8. The LCP of claim 7, wherein the additional parameter is one or more of a cardiovascular pressure, a heart sound, an ECG attribute, a blood flow, impedance, respiration, and/or one or more cardiac dimensions.

9. A medical device system, comprising:
   a first implantable medical device including a gyroscope, the first implantable medical device configured to be secured to a patient's heart;
   a second medical device in communication with the first implantable medical device;
   the first implantable medical device and/or the second medical device configured to:
      determine a twisting profile of the patient's heart based at least in part on data obtained from the gyroscope of the first implantable medical device;
      adjust one or more therapy parameters of a therapy based at least in part on the twisting profile; and
      deliver the therapy using one or more of the adjusted therapy parameters.

10. The medical device system of claim 9, wherein the twisting profile comprises a twist velocity, a twist vector, and a twist angle.

11. The medical device system of claim 9, wherein the twisting profile provides confirmation of an event detected by the second medical device.

12. The medical device system of claim 9, wherein the first implantable medical device and/or the second medical device are further configured to update the twisting profile at a predefined regular interval.

13. The medical device system of claim 9, wherein the first implantable medical device and/or the second medical device are further configured to update the twisting profile in response to a detected condition change.

14. The medical device system of claim 13, wherein the detected condition change corresponds to one of exercise, heart failure status, or posture.

15. A method for monitoring cardiac dysfunction of a patient's heart using a leadless cardiac pacemaker (LCP) secured to the patient's heart, wherein the LCP includes a housing, an electrode secured relative to the housing and exposed to an environment outside of the housing, and a gyroscope disposed relative to the housing, comprising:
    delivering a therapy to the patients' heart using the LCP;
    determining a twisting profile over one or more cardiac cycles based at least in part on data obtained from the gyroscope of the leadless cardiac pacemaker (LCP);
    adjusting one or more therapy parameters of a therapy for the patient's heart based at least in part on the twisting profile; and
    delivering the adjusted therapy to the patient's heart using the LCP.

16. The method of claim 15, wherein the twisting profile includes at least one of a twist angle, a twist vector, and a twist velocity.

17. The method of claim 15, wherein adjusting one or more therapy parameters comprises adjusting an implant location of the LCP.

18. The method of claim 15, wherein adjusting one or more therapy parameters comprises adjusting an AV delay.

19. The method of claim 15, wherein adjusting one or more therapy parameters comprises adjusting a VV delay.

20. The method of claim 15, wherein adjusting one or more therapy parameters comprises delivering an ATP therapy using the LCP when the twisting profile indicates a tachyarrhythmia that is treatable with ATP therapy.

\* \* \* \* \*